(12) United States Patent
Moreno et al.

(10) Patent No.: US 11,653,635 B2
(45) Date of Patent: *May 23, 2023

(54) METHODS FOR INCREASING GENETIC PROGRESS IN A LINE OR BREED OF SWINE USING SEX-SELECTED SPERM CELLS

(71) Applicant: Inguran, LLC, Navasota, TX (US)

(72) Inventors: Juan Moreno, Navasota, TX (US);
Gregg Bevier, Navasota, TX (US);
John Dobrinsky, Oregon, WI (US)

(73) Assignee: Inguran, LLC, Navasota, TX (US)

( * ) Notice: Subject to any disclaimer, the term of this patent is extended or adjusted under 35 U.S.C. 154(b) by 726 days.

This patent is subject to a terminal disclaimer.

(21) Appl. No.: 16/708,007

(22) Filed: Dec. 9, 2019

(65) Prior Publication Data

US 2020/0146268 A1 May 14, 2020

Related U.S. Application Data

(63) Continuation of application No. 16/248,569, filed on Jan. 15, 2019, now Pat. No. 10,542,734, which is a continuation of application No. 15/655,663, filed on Jul. 20, 2017, now Pat. No. 10,188,082, which is a continuation of application No. 14/406,186, filed as application No. PCT/US2013/044521 on Jun. 6, 2013, now Pat. No. 9,743,645, which is a continuation of application No. 13/840,598, filed on Mar. 15, 2013, now Pat. No. 9,433,195.

(60) Provisional application No. 61/656,446, filed on Jun. 6, 2012.

(51) Int. Cl.
| | |
|---|---|
| *A01K 67/00* | (2006.01) |
| *A01K 67/02* | (2006.01) |
| *A61D 19/02* | (2006.01) |
| *A61B 34/20* | (2016.01) |
| *G16B 20/40* | (2019.01) |
| *A61B 1/04* | (2006.01) |
| *A61B 1/015* | (2006.01) |
| *A61B 1/303* | (2006.01) |
| *A61B 1/313* | (2006.01) |
| *A61B 8/08* | (2006.01) |
| *A61B 10/00* | (2006.01) |
| *A61M 31/00* | (2006.01) |
| *G16B 20/00* | (2019.01) |

(52) U.S. Cl.
CPC .............. *A01K 67/02* (2013.01); *A61B 1/015* (2013.01); *A61B 1/04* (2013.01); *A61B 1/303* (2013.01); *A61B 1/313* (2013.01); *A61B 8/08* (2013.01); *A61B 10/0012* (2013.01); *A61B 34/20* (2016.02); *A61D 19/027* (2013.01); *A61M 31/002* (2013.01); *G16B 20/40* (2019.02); *A01K 2227/108* (2013.01); *A61B 2034/2057* (2016.02); *G16B 20/00* (2019.02)

(58) Field of Classification Search
None
See application file for complete search history.

(56) References Cited

U.S. PATENT DOCUMENTS

| | | |
|---|---|---|
| 5,651,330 A | 7/1997 | Jewett |
| 6,071,689 A | 6/2000 | Seidel |
| 6,149,867 A | 11/2000 | Seidel |
| 6,263,745 B1 | 7/2001 | Buchanan |
| 6,357,307 B2 | 3/2002 | Buchanan |
| 6,372,422 B1 | 4/2002 | Seidel |
| 6,524,860 B1 | 2/2003 | Seidel |
| 6,604,435 B2 | 8/2003 | Buchanan |
| 6,617,107 B1 | 9/2003 | Dean |
| 6,695,767 B2 | 2/2004 | Garcia et al. |
| 6,746,873 B1 | 6/2004 | Buchanan |
| 6,782,768 B2 | 8/2004 | Buchanan |
| 6,819,411 B1 | 11/2004 | Sharpe |
| 7,094,527 B2 | 8/2006 | Seidel |
| 7,169,548 B2 | 1/2007 | Maxwell |
| 7,195,920 B2 | 3/2007 | Seidel |
| 7,208,265 B1 | 4/2007 | Schenk |
| 7,221,453 B2 | 5/2007 | Sharpe |
| 7,325,690 B2 | 2/2008 | Cognard |
| 7,335,507 B2 | 2/2008 | Anzar |
| 7,371,517 B2 | 5/2008 | Evans |
| 7,586,604 B2 | 9/2009 | Sharpe |
| 7,618,770 B2 | 11/2009 | Schenk |
| 7,713,687 B2 | 5/2010 | Seidel |
| 7,723,116 B2 | 5/2010 | Evans |

(Continued)

FOREIGN PATENT DOCUMENTS

| | | |
|---|---|---|
| EP | 1017987 B1 | 6/2005 |
| EP | 1554180 B1 | 1/2007 |

(Continued)

OTHER PUBLICATIONS

Martinez, E.A., et al., "Successful non-surgical deep intrauterine insemination with small numbers of spermatozoa in sows", Reproduction-online Aug. 2001, 122 289-296.

Martinez, E.A., et al., "An update on reproductive technologies with potential short-term application in pig production", Reprod Domest Anim. Aug. 2005; 40(4): 300-9.

Martinez, E.A., et al., "Minimum number of spermatozoa required for normal fertility after deep intrauterine insemination in non-sedated sows", Reproduction, Jan. 1, 2002, 123 163-170.

(Continued)

*Primary Examiner* — Marcia S Noble
(74) *Attorney, Agent, or Firm* — Ryan Christensen; Hashim Rahman (57) ABSTRACT

The invention relates to methods of increasing the genetic progress of a line, breed or herd of swine through the use of sex-selected sperm cells in artificial insemination techniques. The invention also encompasses methods of artificially inseminating a swine via deep intrauterine catheter or via a laparoscopic procedure, which allow the use of reduced doses of sex-selected sperm cells.

8 Claims, 1 Drawing Sheet

(56) References Cited

U.S. PATENT DOCUMENTS

| | | |
|---|---|---|
| 7,758,811 B2 | 7/2010 | Durack |
| 7,771,921 B2 | 8/2010 | Seidel |
| 7,799,569 B2 | 9/2010 | Durack |
| 7,820,425 B2 | 10/2010 | Schenk |
| 7,833,147 B2 | 11/2010 | Graham |
| 7,838,210 B2 | 11/2010 | Ludwig |
| 7,855,078 B2 | 12/2010 | Evans |
| 7,892,725 B2 | 2/2011 | Graham |
| 7,893,315 B2 | 2/2011 | Chung et al. |
| 7,929,137 B2 | 4/2011 | Sharpe |
| 7,943,384 B2 | 5/2011 | Durack |
| 7,981,682 B2 | 7/2011 | Evans |
| 7,998,700 B2 | 8/2011 | Ludwig |
| 8,060,353 B2 | 11/2011 | Salinas |
| 8,080,422 B2 | 12/2011 | Neas |
| 8,338,098 B2 | 12/2012 | Khatib et al. |
| 2005/0245902 A1 | 11/2005 | Cornish et al. |
| 2008/0028478 A1 | 1/2008 | Buttram et al. |
| 2012/0295247 A1 | 11/2012 | Liegeois |
| 2012/0301868 A1 | 11/2012 | Pascual |
| 2013/0331693 A1 | 12/2013 | Moreno et al. |

FOREIGN PATENT DOCUMENTS

| | | |
|---|---|---|
| EP | 1608382 B1 | 8/2007 |
| EP | 1044262 B1 | 10/2008 |
| EP | 1608963 B1 | 12/2009 |
| EP | 1730523 B1 | 1/2010 |
| EP | 1238261 B1 | 5/2010 |
| EP | 1546325 B1 | 8/2011 |
| WO | 03096799 A2 | 11/2003 |
| WO | 2004088283 A2 | 10/2004 |
| WO | 2010034871 A1 | 1/2010 |
| WO | 2010025404 A1 | 3/2010 |
| WO | 2010124220 A1 | 10/2010 |
| WO | 2012002823 A2 | 5/2012 |

OTHER PUBLICATIONS

Martinez, E.A. , et al. "Incidence of Unilateral Fertilizations after Low Dose Deep Intrauterine Insemination in Spontaneously Ovulating Sows under Field Conditions", Reproduction in Domestic Animals, vol. 41, Issue1, pp. 41-47, Feb. 2006.

Medeiros, CM, et al., Current status of sperm cryopreservation: why isn't it better? Theriogenology, Jan. 1, 2002; 57(1): 327-44.

Rath, D., et al. "Birth of female piglets following intrauterine insemination of a sow using flow cytometrically sexed boar semen", Veterinary Record 2003: 152: 13 400-401.

Roca, Jordi, et al. "Fertility of weaned sows after deep intrauterine insemination with a reduced number of frozen-thawed spermatozoa", Theriogenology, vol. 60, Issue 1, Jun. 2003, pp. 77-87.

Tummaruk, P., et al., "Distribution of Spermatozoa and Embryos in the Female Reproductive Tract after Unilateral Deep Intra Uterine Insemination in the Pig", Reproduction in Domestic Animals, vol. 42, Issue 6, pp. 603-609, Dec. 2007.

Vazquez, Juan, M. et al., "Birth of piglets after deep intrauterine insemination with low cytometrically sorted boar spermatozoa", Theriogenology, vol. 59, Issue 7, Apr. 2003, pp. 1605-1614.

Vazquez, J.M., et al. "New developments in low-dose insemination technology", Theriogenology, vol. 70(8): Nov. 2008, pp. 1216-1224.

Wongtawan, Tuempong, et al., "Fertility after deep intra-uterine artificial insemination of concentrated low-volume boar semen doses", Theriogenology, vol. 65, Issue 4, Mar. 2006, pp. 773-787.

WIPO International Search Report and Written Opinion dated Jan. 14, 2014, issued in related PCT Application No. PCT/US13/44521 (45 pp).

Garcia, E.M., et al. "Improving the fertilizing ability of sex sorted boar spermatozoa", Theriogenoloy 68, (2007) 771-778.

Garner, Duane, "Flow cytometric sexing of mammalian sperm", Theriogenology 65 (2006) 943-957.

Dimitrov, S., et al. "Deep Intrauterine and Transcervical Insemination of Sows and Gilts", Trakia Journal of Sciences, vol. 5, No. 1, 2007, pp. 40-46.

Caballero, I., et al., "PSP-I/PSP-II spermadhesin exert a decapacitation effect on highly extended boar spermatozoa", Int. Jour. of Andrology 32, 505-513 (2008).

Ekhlasi-Hundrieser, M., et al., "point mutations abolishing the mannose-binding capability of boar spermadhesin AQN-1", Biochimica et Biophysica Acta 1784 (2008) 856-862.

Garcia, E.M., et al., "Localization and expression of spermadhesin PSP-1/PSP-II subunits in the reproductive organs of the boar" Int. Journal of Andrology 31, 408-417 (2007).

Romero, A., et al., "X-Ray Crystallographic Analysis of Boar PSP-I/PSP-II Complex A Zona Pellucida-Binding Protein", The Fate of the Male Germ Cell, Plenum Press, New York 1997, pp. 311-312.

Silva, L.D.M., et al. Laparoscopic Intrauterine Insemination In The Bitch, Theriogenology, 995, vol. 43, pp. 615-623.

PCT International Search Report and Written Opinion dated Feb. 11, 2014, issued in corresponding PCT Application No. PCT/US2013/072272 (13 pp).

Johnson, L.A., Sex Preselection In Swine: Altered Sex Ratios In Offspring Following Surgical Insemination Of Flow Sorted X-And Y-Bearing Sperm, Reproduction in Domestic Animals, 1991, vol. 26; pp. 309-314.

Roberts, E., et al., A Study Of Hybrid Vigor In A Cross Between Poland China and Duroc Jersey Swine. Journal of Agricultural Research, 1939, vol. 59; pp. 847-854.

Long, T.E, et al., "Estimating Genetic Merit. National Swine Improvement Federation (NSIF)" Swine Genetics Fact Sheet No. 8, 2003, pp. 1-4.

Vazquez, J.M., et al. "Low-Dose Insemination In Pigs: Problems And Possibilities", Reproduction In Domestic Animals, 2008, vol. 43, pp. 347-354.

Martinez, E.A., et al., "Successful Non-Surgical Deep Intrauterine Insemination With Small Numbers Of Spermatozoa In Sows", Reproduction, 2001, vol. 122, pp. 289-296.

Schalla, S, et al., "Magnetic Resonance-Guided Cardiac Catheterization In A Swine Model Of Atrial Septal Defect", Circulation 2003, vol. 108, pp. 1865-1870.

Blair, R.M., et al., Peri-oestrous hormone profiles, embryonic survival and variation in embryonic developments in gilts and primiparous sows, Journal of Reproduction and Fertility , 101, 167-173 (1994).

Dally, M.R., et al., Laparoscopic Artificial Insemination A Means to Improve Genetics Wool Production School, pp. 64-67 (1992).

"Embryo and cloning technologies for custom genetic livestock production", Minitube, 1pp.

"Frozen-Thawed Semen", 1 pp.

Garner, D.L., et al., "Viability Assessmnet of Mammalian Sperm Using SYBR-14 and Propidium Iodide", Biology of Reproduction, vol. 53, 276-284 (1995).

Gil, M.A., et al., "Pentoxifylline added to freezin or post-thaw extenders does not improve the survival or in vitro fertilising capacity of boar spermatozoa", Society for Reproduction and Fertility, Reproduction Mar. 1, 2010 139 557-564.

Gosalvez.L.F., et al., "Assessment of suitable porcine semen for freezing, according to the ejaculate characteristics in the Iberico x Landrace breed", Reproduction in Domestic Animals, 2002: 37(5): 282-4, Abstract 1pp.

IMV Technologies Catalog "Biotechnologies for pig reproduction", www.imv-technologies.com, 28pp.

Johnson, L.A., et al., "Use of Boar Spermatozoa for Artificial Insemination III. fecundity of Boar Spermatozoa Stored in Beltsville Liquid and Kiev Extenders for Three Days at 18C", Journal of Animal Science, 1982, 54: 132-136.

Kamp, G., et al. "Energy metabloism and intracellular pH in boar spermatozoa", Society for Reproduction and Fertility, 126, pp. 517-525 (2003).

Klinc, P., et al., "Reduction of Oxidative Stress in Bovine Spermatozoa During Flow Cytometric Sorting", Reproduction in Domestic Animals, vol. 42, pp. 63-67 (2007).

(56) References Cited

OTHER PUBLICATIONS

Knox, R., et al., "An update on North American Boar stud practices", Theriogenology, vol. 70, pp. 1202-1208, (2008).
Marin, et al., "Metabolic strategy of boar spermatozoa revealed by a metabolomic characterization", FEBS Letters, vol. 554, Issue 3, Nov. 20, 2003, pp. 342-346.
Martelli, A., et al., "Blood vessel remodeling in pig ovarian follicles during the periovulatory period: an immunohistochemisty and SEM-corrosion casting study", Reproductive Biology and Endocrinology, 2009, 7:72 (2009).
Medrano, A., "Variations in the Proportion of Glycolytic/Non-glycolytic Energy Substrates Modulate Sperm Membrane Integrity and Function in Diluted Boar Samples Stored at 15-17° C.", Reproduction in Domestic Animals, vol. 40, pp. 448-453, (2005).
Rath, D., "Production of Piglets Preselected for Sex Following In Vitro Fertilization with X and Y Chromosome-Bearing Spermatozoa Sorted By Flow Cytometry", Theriogenology, vol. 47 pp. 795-800 (1997).
Rath, D., "Low Dose Insemination the the Sow—A Review", Reproduction in Domestic Animals, vol. 37, pp. 201-205 (2002).
Roca, J. et al., "Survival and Fertility f Boar Spermatozoa After Freeze-Thawing in Extender Supplemented With Butylatd Hydroxytoluene", Journal of Andrology, vol. 25, No. 3 pp. 397-405 (2004).
Rodriguez-Gil, J.E., Mammalian Sperm Energy Resources Management and Survival during Conservation in Refrigeration.
Rodriguez-Martinez, H., et al. "Advances in Boar Semen Cryopreservation", Veterinary Medicine International, vol. 2011, Article ID 396181, 5pp. (2011).
Salisbury, G. W, et al., "Substrate-Free Epididymal-Like Bovine Spermatozoa", Journal of Reproduction and Fertility vol. 6, pp. 351-359, (1963).
Spinaci, M., "Sperm Sorting Procedure Induces a Redistribution of Hsp70 but Not Hsp60 and Hsp90 in Boar Spermatozoa", Journal of Andrology, vol. 70, No. 6, pp. 899-907 (2006).
Sonesson, A., et al., "Mating schemes for optimum contribution selection with constrained rates of inbreeding", Genetics Selection Evolution, 32 (2000) 231-248.
Woolliams, J.A., et al., "Decision rules and variance of response in breeding schemes", Animal Production, vol. 56, Issue 02, Apr. 1993, pp. 179-186.
Meuwissen, T.H., "Maximizing the response of selection with a predefined rate of inbreeding", Journal of Animal Science, vol. 75 No. 4, Apr. 1997, 934-940.
Vasquez, J.M., et al., "Sex-sorting sperm by flow cytometry in pigs: Issues and perspectives", Theriogenology, vol. 71, pp. 80-88 (2009).
U.S. Office Action dated Mar. 26, 2015, issued in related U.S. Appl. No. 13/840,598.
U.S. Office Action dated Mar. 10, 2016 in related U.S. Appl. No. 13/840,598.
Bathgate et al: "Non-Surgical Deep Intra-Uterine Transfer of In Vitro Produced Porcine Embryos Derived From Sex-Sorted Frozen-Thawed Boar Sperm", Animal Reproduction Science, Feb. 2007, vol. 99, No. 1-2, Apr. 26, 2006 (Apr. 26, 2006), pp. 82-92.
Korean Notification of Provisional Rejection dated Dec. 18, 2015 in related KR Appl. No. 10-2014-14964.
Supplementary European Search Report dated Jan. 22, 2016 in related EP Appl. No. 13800545.9.
Johnson L A et al: "Preselection of Sex of Offspring in Swine for Production: Current Status of the Process and its Application", Theriogenology, vol. 63, No. 2, Jan. 15, 2005, pp. 615-624.
Roca, J, et al. "Approaches Towards Efficient Use of Boar Semen in the Pig Industry ", Reprod Domest Anim. Sep. 2011; vol. 46, Suppl 2, Aug. 26, 2011, pp. 79-83.
Gerrits R J et al: "Perspectives for Artificial Insemination and Genomics to Improve Global Swine Populations", Theriogenology, vol. 63, No. 2, Jan. 15, 2005 (Jan. 15, 2005), pp. 283-299.
D Rath et al: "Application and Commercialization of Flow Cytometrically Sex-Sorted Semen", Reproduction in Domestic Animals, vol. 43, Jul. 1, 2008 (Jul. 1, 2008), pp. 338-346.
Robinson J A B et al: "Impact of Genetic Selection on Management of Boar Replacement", Theriogenology, vol. 63, No. 2, Jan. 15, 2005 (Jan. 15, 2005), pp. 668-678.
Korean Notice of Decision to Grant dated Jan. 3, 2017 in related KR Appl. No. 10-2014-7034384.
U.S. Final Office Action dated Nov. 16, 2016 in related U.S. Appl. No. 14/406,186.
Canadian Examination Report dated Jan. 21, 2016 in related CA Appl. No. 2875058.
New Zealand Examination Report dated Mar. 2, 2016 in related NZ Appl. No. 630356.
Chilean Office Acton dated Mar. 16, 2017 in related CL Appl. No. 3341-2014.
Chilean Office Acton dated Mar. 29, 2017 in related CL Appl. No. 2365-2015.
EP Examination Report dated Jun. 30, 2017 in related EP Appl. No. 13800545.9.
Abdel-Azim G et al: "Genetic Impacts of Using Female-Sorted Semen in Commercial and Nucleus Herds", Journal of Dairy Science, vol. 90, No. 3, Mar. 1, 2007, pp. 1554-1563.
U.S. Notice of Allowance dated Apr. 21, 2017 in related U.S. Appl. No. 14/406,186.
Chinese Examination Report dated May 4, 2016 in related CN Appl. No. 201380029461.5.
Canadian Examination Report dated Jun. 20, 2016 in related CA Appl. No. 2904193.
U.S. Notice of Allowance dated Jul. 21, 2016 in related U.S. Appl. No. 13/840,598.
European Extended Search Report dated Aug. 24, 2016 issued in EP Appl. No. 13877728.9.
Korean Provisional Rejection dated Jul. 29, 2016 issued in KR Appl. No. 10-2014-7034384.
Canadian Office Action dated Aug. 7, 2017 issued in related CA Appl. No. 2,904,193.
Canadian Office Action dated Aug. 4, 2017 issued in related CA Appl. No. 2,875,058.
U.S. Office Action dated Jul. 13, 2015, issued in related U.S. Appl. No. 13/840,598.
NZ Office Action dated Aug. 21, 2015, issued in related application No. 630356.
Chilean Office Action dated Oct. 13, 2017 issued in related CL Appl. No. 201502365.
Chinese Patent Examination Report dated Sep. 24, 2015 in related CN Appl. No. 201380029461.5.
U.S. Final Office Action dated Feb. 11, 2016 in related U.S. Appl. No. 14/090,979.
U.S. Office Action dated Jun. 28, 2016 in related U.S. Appl. No. 14/090,979.
U.S. Final Office Action dated Dec. 19, 2016 in related U.S. Appl. No. 14/090,979.
U.S. Notice of Allowance dated Oct. 6, 2017 in related U.S. Appl. No. 14/090,979.
Chilean Office Acton dated Dec. 28, 2017 in related CL Appl. No. 3341-2014.
U.S. Office Action dated May 17, 2018 in related U.S. Appl. No. 15/853,010.
Mexican Examination Report dated Mar. 13, 2018 issued in related MX Appl. No. MX/a/2014/015000.
Mexican Examination Report dated Mar. 13, 2018 issued in related MX Appl. No. MX/a/2014/012648.
European Invitation pursuant to Rule 137(4) dated Apr. 16, 2018 issued in EP Appl. No. 13877728.9.
Canadian Requisition by the Examiner dated Jun. 26, 2018 in related CA Application No. 2,904,193.
Chinese Office Action dated Jul. 17, 2018 in related CN Application No. 201380074208.1.
Mexican Notice of Allowance dated Jul. 3, 2018 in related MX Application No. MX/a/2014/015000.
Mexican Notice of Allowance dated Jul. 3, 2018 in related MX Application No. MX/a/2014/012648.
Canadian Requisition by the Examiner dated Jul. 9, 2018 in related CA Application No. 2,875,058.

(56) References Cited

OTHER PUBLICATIONS

Bergstrom et al., "Effects of Feeder Design, Gender, and Dietary Concentration of Dried Distillers Grains with Solubles on the Growth Perfomance and Carcass Characteristics of Growing-Finishing Pigs" Report of progress 2009, Kansas State University Agricultural Experiment Station and Cooperative Extension Services, 1020.

Knox, Robert V., "The Anatomy & Physiology of Sperm Production in Boars" University of Illinois, Department of Animal Sciences, 2002, pp. 1-11.

Donadeu, Meritxell, "All you ever wanted to know about boar semen." The Pig Site, 2006, http://www.thepigsite.com/articles/1825/all-you-ever-wanted-to-know-about-boar-semen, Retrieved on Jun. 18, 2012.

Roca et al., "Approached Towards Efficient Use of Boar Semen in the Pig Industry" Reprod Dom Anim, 2001, 46, Suppl 2, 79-83.

Rath et al., "Application and Commercialization of Flow Cytometrically Sex-Sorted Semen" Reprod Dom Anim, 2008, 43, Suppl. 2, 338-346.

Rath et al., "Low Dose Insemination Technique in the Pig" IVth Intl Conference on Boar Semen Preservation, Beltsville, Maryland, 2000, pp. 115-118.

Foote, R.H., "Buffers and Extenders: What Do They Do? Why Are They Important?" Proc of the NAAB Tech. Conf. On Artificial Insemination and Reproduction, 62-70 (1984).

Van Wienen et al., "Single Layer Centrifugation with Androcoll-P Can Be Scaled-Up to Process Larger Volumes of Boar Semen." ISRN Veterinary Science, vol. 2011, Article ID 548385, 8 pages.

Rath, D., "Low Dose Insemination in the Sow—A Review" Reprod Dom Anim, 2002, 37, 201-205.

"Guidlines for Uniform Swine Improvement Programs—On-Farm Programs" National Swine Improvement Federation, 1976 revised in 1987 and 1996, http://www.nsif.com/guidel/ONFARM.HTM,pp. 1-9.

Almond, Glen W., "Synchronization of Estrus In Gilts" Proc of the North Carolina Healthy Hogs Seminar, 1997, http://www.ncsu.edu/project/swine_extension/healthyhogs/book1997/almond2.htm, pp. 1-3.

Mathur, P.K., "Effective selection to expedite your genetic progress" Canadian Centre for Swine Improvement Inc., 2002, http://www.ccsi.ca/main.cfm?target_page=select, 7 pages.

Grossfeld et al., "Production of piglets with sexed semen employing a non-surgical insemination technique" Theriogenology, 2005, 63, pp. 2269-2277.

Gil et al., "Morphometry of porcine spermatozoa and its functional significance in relation with the motility parameters in fresh semen" Theriogenology, 2009, 71, 254-263.

Chae et al., "Abnormal gene expression in extraembryonic tissue from cloned porcine embryos" Theriogenology, 2009, 71,323-333.

Rath et al., "In Vitro Production of Sexed Embryos for Gender Preselection: High-Speed Sorting of X-Chromosome Bearing Sperm to Produce Pigs After Embryo Transfer" J. Anim. Sci, 1999, 77, 3346-3352.

Abeydeera et al., "Birth of Piglets Preselected for Gender Following in Vitro Fertilization of in Vitro Matured Pig Oocytes by X and Y Chromosome Bearing Spermatozoa Sorted by High Speed Flow Cytometry" Theriogenology, 1998, 50, 981-988.

Aviles-Lopez et al., "Differences in Tyrosine Phosphorylation in Epididymal and Ejaculated Boar Spermatozoa" Reprod Dom Anim, 2011, 46, 78-161, The 15th Annual Conference of the ESDAR, Abstract P35.

De Ondiz et al., "Immunolocalization Pattern of a-L-fucosidase in Porcine Sperm" Reprod Dom Anim, 2011, 46, 78-161, The 15th Annual Conference of the ESDAR, Abstract P69.

Del Olmo., "The Effect of Butylated Hydroxytoluene on the Functionality of Boar Spermatozoa Undergoing Sex Sorting and Cryopreservation" Reprod Dom Anim, 2011, 46, 78-161, The 15th Annual Conference of the ESDAR, Abstract P73.

Gomis Almendro et al., "Forskolin Improves Vitrification Ability of In Vivo Derived Porcine Zygotes" Reprod Dom Anim, 2011, 46, 78-161, The 15th Annual Conference of the ESDAR, Abstract P109.

Martinez et al., "Effect of Pentoxifylline on Motility Pattern of Fresh Boar Spermatozoa" Reprod Dom Anim, 2011, 46, 78-161, The 15th Annual Conference of the ESDAR, Abstract P171.

Maside et al., "Exposure of Porcine in Vitro Matured Oocytes to SYBR 14 and Fluorescence Limits their Developmental Competence" Reprod Dom Anim, 2011, 46, 78-161, The 15th Annual Conference of the ESDAR, Abstract P173.

Matas et al., "Effect of a-L Fucosidase on P-Tyrosine Phosphorylation of Boar Sperm" Reprod Dom Anim, 2011, 46, 78-161, The 15th Annual Conference of the ESDAR, Abstract P175.

Parrilla et al., "Post-Thaw Quality of Boar Semen Frozen at Low Sperm Concentration" Reprod Dom Anim, 2011, 46, 78-161, The 15th Annual Conference of the ESDAR, Abstract P208.

Romero et al., "Preliminary Study on the Roles of a-LFucosidase on Porcine In vitro Fertilization" Reprod Dom Anim, 2011, 46, 78-161, The 15th Annual Conference of the ESDAR, Abstract P234.

Romero et al., "Addition of a-L-Fucosidase to the Porcine In vitro Fertilization Medium Increases Penetration Rates" Reprod Dom Anim, 2011, 46, 78-161, The 15th Annual Conference of the ESDAR, Abstract P235.

Maside et al., "Effects of Hoechst 33342 staining and ultraviolet irradiation on developmental competence of in vitro matured porcine oocytes" Reprod Dom Anim, 2010, vol. 45, pp. 79-102, 2010 Congress of the Spanish Society of Animal Reproduction, Oral Communication 13.

Juarez et al., "The effect of ultra-rapid cooling rate from 17 to 5° C. in inter-boar sperm cryosurvival" Reprod Dom Anim, 2010, vol. 45, pp. 79-102, 2010 Congress of the Spanish Society of Animal Reproduction, abstract P49.

De Ondiz et al., "Sperm a-L-Fucosidase inhibition improved monospermy rate in porcine IVF" Reprod Dom Anim, 2010, vol. 45, pp. 79-102, 2010 Congress of the Spanish Society of Animal Reproduction, abstract P50.

Del Olmo et al., "Influence of seminal plasma and heterodimer PSP-I/PSP-II on the kinematic charges of boar sperm undergoing sex sorting and cryopreservation" Reprod Dom Anim, 2010, vol. 45, pp. 79-102, 2010 Congress of the Spanish Society of Animal Reproduction, abstract P58.

Gomis et al., "Effect of warming in syringe on survival of SOPS-vitrified in vivo derived porcine embryos" Reprod Dom Anim, 2010, vol. 45, pp. 79-102, 2010 Congress of the Spanish Society of Animal Reproduction, abstract P61.

Sanchez-Osorio et al., "Intraoviductal laparoscopic transfer of porcine somatic cell nuclear transfer embryos" Reprod Dom Anim, 2010, vol. 45, pp. 79-102, 2010 Congress of the Spanish Society of Animal Reproduction, abstract P62.

Del Olmo, "DNA fragmentation in sex-sorted, frozen-thawed boar sperm" Reprod in Domestic Animals, 2011; 46 (supplement 2), 109, 7th International Conference on Boar Semen Preservation, Abstract P54.

Parrilla et al., "Membrane lipid peroxidation in boar spermatozoa subjected to different handlings" Reprod in Domestic Animals, 2011; 46, 89, The 15th Annual Conference of the ESDAR, 0C15.

Maside et al., "Brief exposure of in vitro matured porcine oocytes stained with Hoechst 33342 to ultraviolet irradiation impairs embryo development" Reprod. in Domestic Animals, 2010; 45, 67, 14th Annual Conference of the European Society for Domestic Animal Reproduction, Abstract No. P20.

Bolarin et al., "Reproductive performance of sows returned to estrus after a DUI insemination" Reprod in Domestic Animals, 2010; 45, 79, 14th Annual Conference of the European Society for Domestic Animal Reproduction, Abstract No. P66.

De Ondiz et al., "Sperm a-D-mannosidase and a-L-fucosidase effect on porcine IVF" Reprod in Domestic Animals, 2010; 45, 84, 14th Annual Conference of the European Society for Domestic Animal Reproduction, Abstract No. P85.

De Ondiz et al., "Effect of the presence of glycosidase inhibitors on porcine embryo development in vitro." Reprod in Domestic Animals, 2010; 45, 84, 14th Annual Conference of the European Society for Domestic Animal Reproduction, Abstract No. P86.

Matas et al., "Selection of boar sperm subpopulations by gradients for increasing the in vitro penetration performance" Reprod in (56) References Cited

OTHER PUBLICATIONS

Domestic Animals, 2010; 45, 98, 14th Annual Conference of the European Society for Domestic Animal Reproduction, Abstract No. P147.
Parrilla et al., "Effect of intra-oviductal laparoscopic manipulation on future reproductive performance of sows" Reprod in Domestic Animals, 2010; 45, 102, 14th Annual Conference of the European Society for Domestic Animal Reproduction, Abstract No. P162.
Parrilla et al., "Insemination with low or very low number of boar spermatozoa undergoing biotechnological treatments" Reprod Dom Anim, 2011, 46 (Suppl. 3), 60-71, The 15th Annual Conference of the ESDAR, Work Shop #10.2.
Garner et al., "Quantification of the X- and Y-Chromosome-Bearing Spermatozoa of Domestic Animals by Flow Cytometry" Biology of Reproduction, 28, 312-321 (1983).
"Methods of Estrus Synchronization For Facilitating Swine Artificial Insemination" Swine Genetics International, http://www.swinegenetics.com/ai_catalog/ai_estrus.html, retrieved Jun. 18, 2012.
Bathgate, et al. "Field fertility of frozen-thawed boar sperm at low doses using non-surgical, deep uterine insemination", Animal Reproduction Science, vol. 103, Issues 3-4, Jan. 2008, pp. 323-335.
Bolarin, A. et al., "Dissimilarities in sows' ovarian status at the insemination time could explain differences in fertility between farms when frozen-thawed semen is used." Theriogenology 2006, 65: 669-680.
Bolarin, et al., "Use of frozen-thawed semen aggravates the summer-autumn infertility of artificially inseminated weaned sows in the Mediterranean region" Journal of Animal Science, 2009, vol. 87, No. 12: 3967-3975.
Fantinati, P., et al., "Laparoscopic insemination technique with low numbers of spermatozoa in superovulated prepuberal gilts for biotechnological application", Theriogenology, Feb. 2005; 63(3): 806-17.
Guthrie, HD, et al., "Impact of storage prior to cryopreservation on plasma membrane function and fertility of boar sperm", Theriogenology, 2005, Jan. 2005; 63 (2): 396-410.
Martinez, E. A., et al., "Deep intrauterine insemination and embryo transfer in pigs", Proceed. of the 6th Int'l Conf. on Pig Reproduction, Univ. Missouri-Columbia, USA, Jun. 2001, pp. 301-311.
U.S. Notice of Allowance dated Oct. 15, 2018 in related U.S. Appl. No. 15/853,010.
U.S. Notice of Allowance dated Sep. 4, 2018 in related U.S. Appl. No. 15/655,663.
Brazilian Office Action dated Nov. 28, 2019 in related BR Application No. BR112014030509-9.
U.S. Office Action dated Apr. 1, 2019 in realted U.S. Appl. No. 16/239,315.
Canadian Requisition by the Examiner dated Aug. 28, 2019 in related CA Application No. 2,875,058.
Canadian Requisition by the Examiner dated Aug. 28, 2019 in related CA Application No. 2,904,193.
Brazilian Office Action dated Oct. 26, 2019 in related BR Application No. BR112015023623-5.
U.S. Office Action dated Apr. 3, 2019 in related U.S. Appl. No. 16/248,569.
U.S. Office Action dated Sep. 22, 2022 in related U.S. Appl. No. 16/747,406.
Chinese Notification of Reexamination dated Aug. 26, 2022 in related CN. Appl. No. 01380074208.1.
European Examination Report dated Aug. 31, 2022 in related EP Appl. No. 13800545.9.
European Examination Report dated Sep. 15, 2022 in related EP Appl. No. 13877728.9.
Brazilian Rejection Decision dated Jan. 25, 2022 in related BR Appl. No. BR112015023623.
Canadian Office Action dated Aug. 17, 2020 issued in related CA Appl. No. 2,875,058.
Canadian Office Action dated Aug. 14, 2020 issued in related CA Appl. No. 2,904,193.
Brazilian Office Action dated Oct. 8, 2020 issued in related BR Appl. No. BR112014030509-9.
Chilean Office Action dated Mar. 30, 2020 issued in related CL Appl. No. 2015002365.
European Office Action dated May 25, 2020 issued in related EP Appl. No. 13800545.9.
Brazilian Office Action dated Apr. 23, 2020 issued in related BR Appl. No. BR112014030509-9.
Brazilian Office Action dated May 11, 2021 issued in related BR Appl. No. 11 2015 023623 5.
Chinese Office Action dated Jan. 5, 2021 issued in related CN Appl. No. 201380074208.1.
Brazilian Office Action dated Oct. 6, 2021 issued in related BR Appl. No. 11 2015 023623 5.
Canadian Office Action dated Sep. 22, 2021 issued in related CA Appl. No. 2875058.
Canadian Office Action dated Sep. 22, 2021 issued in related CA Appl. No. 2904193.

METHODS FOR INCREASING GENETIC PROGRESS IN A LINE OR BREED OF SWINE USING SEX-SELECTED SPERM CELLS

This application is a continuation of U.S. application Ser. No. 16/248,569, filed on Jan. 15, 2019, which itself is a continuation of U.S. application Ser. No. 15/655,663, filed on Jul. 20, 2017, now U.S. Pat. No. 10,188,082, issued Jan. 29, 2019, which itself is a continuation of U.S. application Ser. No. 14/406,186, filed on Dec. 5, 2014, now U.S. Pat. No. 9,743,645, issued Aug. 29, 2017, which itself is a national stage entry of International Application No. PCT/US2013/044521, filed Jun. 6, 2013, which itself claims priority to U.S. application Ser. No. 13/840,598 filed Mar. 15, 2013, now U.S. Pat. No. 9,433,195, issued Sep. 6, 2016, and U.S. Provisional Application No. 61/656,446, filed on Jun. 6, 2012.

FIELD OF THE INVENTION

The invention relates to methods of increasing the genetic progress of a line, breed or herd of swine through the use of sex-selected sperm cells in artificial insemination techniques. The invention also encompasses methods of artificially inseminating a swine via deep intrauterine catheter or via a laparoscopic procedure, which allow the use of reduced doses of sex-selected sperm cells.

BACKGROUND

There is a need in the swine industry to increase the rate of desirable genetic change in lines and breeds as well as to lower operational costs on breeding and commercial swine farms. The inventions disclosed herein achieve these goals by allowing the operator of a breeding or commercial farm to select the sex of offspring swine using sex-selected sperm cell samples and/or by allowing the use of far fewer genetically superior boars through the use of reduced sperm cell doses for artificial insemination procedures via deep intrauterine catheter or laparoscopy.

SUMMARY OF THE INVENTION

One embodiment of the present invention comprises a method of increasing the genetic progress of a line or breed of swine comprising collecting a semen sample from a boar from said line or breed; sorting said semen sample into at least two subpopulations of sperm cells, wherein at least 80% of a first subpopulation bears X-chromosomes or Y-chromosomes; inseminating a sow from said line or breed with sperm cells from said first subpopulation; producing one or more offspring from said sow; calculating a selection index for one or more of said offspring; and selecting one or more of said offspring having a higher selection index compared to the average selection index for said line or breed to breed with a swine from said line or breed so as to increase the genetic progress of said line or breed.

Another embodiment of the invention comprises a method of increasing the genetic progress of a line or breed of swine comprising collecting a semen sample from a boar from said line or breed; sorting said semen sample into at least two subpopulations of sperm cells, wherein at least 80% of a first subpopulation bears X-chromosomes or Y-chromosomes; inseminating a sow from said line or breed with sperm cells from said first subpopulation; producing one or more offspring from said sow; obtaining a value for a trait in one or more of said offspring; and selecting one or more of said offspring having a value for said trait that is greater than or less than the average value for said trait in said line or breed to breed with a swine from said line or breed so as to increase the genetic progress of said line or breed.

In some embodiments of the invention, semen samples to be used with the invention are sorted into at least two subpopulations of sperm cells, wherein at least 60%, 60-65%, 65%, 65-70%, 70%, 70-75%, 75%, 75-80%, 80%, 80-85%, 85%, 85-90%, 90%, 90-95%, 95%, 95-99% or about 99% of a first subpopulation bears X-chromosomes and/or Y-chromosomes.

Another method for increasing the genetic progress of a line or breed of swine comprises preparing one or more embryos or zygotes, either in vivo or in vitro, using a sex-selected sperm cell sample obtained from a boar of said line or breed, and then transferring said one or more embryos or zygotes, by any method known in the art, into a sow for gestation. In certain aspects of the invention, the egg donor is a sow from a line or breed. In some specific embodiments of the invention, the embryo or zygote is transferred into or out of a sow using a deep intrauterine catheter or laparoscopy. This method can also further comprise the steps of calculating a selection index for one or more of the offspring produced from said embryo or zygote; selecting one or more of said offspring based on said one or more offspring having a higher selection index compared to the average selection index for said line or breed; using said one or more offspring having a higher selection index compared to the average selection index for said line or breed to breed with a swine from the same line or breed so as to increase the selection intensity of that line or breed. Another embodiment of the invention comprises using such embryos or zygotes to repopulate a line, breed and/or herd.

Another aspect of the invention comprises selecting an embryo or zygote for use in the invention based on the presence or absence of a genetic marker in the embryo or zygote. In certain embodiments, such a genetic marker can be screened for by removal of one or more blastomeres from the embryo or zygote and testing said one or more blastomeres for the presence or absence of said genetic marker. The genetic marker can be a marker for, or associated with, for example, any of the swine traits disclosed herein. In certain embodiments, one or more blastomeres are removed from the embryo or zygote at the 4-16 cells stage, the 4-10 cell stage or the 4-8 cells stage. Any technique known in the art can be used for removal of a blastomere from an embryo or zygote, including but not limited to those disclosed in U.S. Pat. No. 7,893,315, the disclosure of which is incorporated by reference herein in its entirety. Briefly, one of the methods described therein comprises immobilizing an embryo and tapping the immobilized embryo until a blastomere is isolated (the embryo can be immobilized using a micropipette and the micropipette holder is tapped to isolate the blastomere). In certain embodiments, screening said embryo or zygote for a genetic marker comprises genotyping a blastomere or cell obtained from said embryo or zygote. Techniques for screening embryos or zygotes for a genetic marker are disclosed in U.S. Pat. No. 8,338,098, the disclosure of which is incorporated by reference herein in its entirety. Briefly, single nucleotide polymorphisms (SNPs) can be identified using the pooled DNA sequencing approach, and then genotyping of the identified SNP can be achieved by a PCR-restriction fragment length polymorphism (PCR-RFLP) based method.

The sorted sperm cells used with the invention constitute "sex-selected" sperm cell samples. Sex-selected sperm cell samples can be derived by any technique known in the art. In one embodiment of the invention, the sex-selected sperm cell samples can be prepared using a flow cytometer. The sex-selected sperm cells for use in any embodiment of the invention can be cryopreserved using any known method and then thawed before use, or alternatively fresh (i.e., never frozen) sex-selected sperm cells can be utilized.

The terms "line" and "breed" mean a group of animals having a common origin and similar identifying characteristics. The instant invention is also applicable to "pure lines" and "pure breeds" of swine, as those terms are used in the art.

The term "selection index" refers to a numerical score generated for an individual swine breed based on the swine's expression of certain traits selected by a breeder. Typically, a breeder will assign a given number of traits, often referred to as selection objects, to each line or breed of swine, and may further differentially weight the importance each trait in generating a selection index. A higher selection index for a swine means that the swine has expressed or carried those traits to a greater degree.

In certain embodiments of the invention, any desirable genotypic or phenotypic trait can be used to construct a selection index for a line or breed of swine. Phenotypic traits that can be utilized in a selection index include, but are not limited to, feed efficiency, average daily gain, carcass lean, carcass quality, fertility, litter size and milk production.

In some embodiments of the invention, the selection index for a particular swine can be calculated using data derived solely from that particular swine in, i.e., individual data, or alternatively, the selection index for a particular swine can be calculated using data derived from a group that contains or is representative of that particular swine, i.e. group data. For example, feed efficiency can be measured in an individual boar—thus, the selection index for the boar in this example would be based on individual data. Alternatively, feed efficiency can be measured for the group of boars housed with the boar in question—the selection index for the boar in this example would be based on group data.

Other aspects of the invention encompass inseminating a sow from said line or breed with sex-selected sperm cells using a deep intrauterine catheter or a needle inserted through a membrane of said sow. Some of these embodiments encompass known surgical and non-surgical techniques that can be used to place sperm cells into a sow's reproductive tract, including laparotomy (surgical procedure involving a large incision through the abdominal wall to gain access into the abdominal cavity). This embodiment contemplates inseminating sows using $1 \times 10^9$ or less total sperm cells.

In other embodiments, a deep intrauterine catheter can be employed to administer a sperm cell sample into distal portions of a sow's reproductive tract such as one or more uterine horns or one or more utero-tubal junctions. In another aspect of the invention, the deep intrauterine catheter is comprised of an outer tube or sheath and an inner flexible probe. In a further aspect of the invention, the flexible inner probe comprises a flexible inner duct through which fluids or cells can pass. In certain embodiments of the invention, the outer tube and inner flexible probe can be made of a plastic, and in other embodiments, they may be made of metal configured to be flexible such as in a coil or spring configuration. In a further embodiment, the deep intrauterine catheter comprises a video camera or scope for visualizing the location of the distal portion of the deep intrauterine catheter within a sow's reproductive tract. In an alternative embodiment, the deep intrauterine catheter can be visualized within the sow's reproductive tract using radiography or fluoroscopy. In another embodiment of the invention, a deep intrauterine catheter can be used to insert or withdraw embryos or zygotes from the distal portions of a sow's reproductive tract such as from one or more uterine horns or from one or more utero-tubal junction.

With respect to insemination with a deep intrauterine catheter, it is contemplated that a dose of $1 \times 10^9$ sperm cells or less is administered to a sow. Such sperm cells may be sex-selected sperm cells. In one embodiment of the invention a dose of sex-selected sperm cells (for instance $600 \times 10^6$, but may be more, or as little as $10 \times 10^6$ if placed in the optimal location at the optimal time of estrus) is administered into one or both uterine horns (e.g., $300 \times 10^6$ sperm cells into each horn) of a sow by deep intrauterine catheter. In other embodiments, doses can vary in the range of or anywhere in between about $300 \times 10^6$, about $150 \times 10^6$, about $140 \times 10^6$, about $100 \times 10^6$, about $70 \times 10^6$, about $50 \times 10^6$, or about $5 \times 10^6$ sex-selected sperm cells or less and can be administered into one or both uterine horns of a sow.

The aforementioned doses can be administered in various volumes, including but not limited to 5 ml for every $150 \times 10^6$ sperm cells, or the same number of cells in a volume in the range of 5 ml, 10 ml, 15 ml, 20 ml, 25 ml, 30 ml or 100 ml, or somewhere between 5-10 ml, 10-20 ml, 20-30 ml, 30-40 ml, 40-50 ml, 50-60 ml, 60-70 ml, 70-80 ml, 80-90 ml or 90-100 ml.

The sex-selected sperm cells for use in any embodiment of the invention can be cryopreserved and then thawed, or alternatively fresh (i.e., never frozen) sex-selected sperm cells can be utilized. The aforementioned doses may also be administered into one or more utero-tubal junctions of a sow.

This embodiment of the invention also encompasses the use of a laparoscope to visualize insertion of a needle through a membrane of a sow for administering a sex-selected sperm cell sample. Both the needle used for injecting the sperm cell sample and the laparoscope, as well as manipulating instruments such as forceps, can be inserted into the abdomen of a sow through small incisions typical of laparoscopic procedures. The invention also encompasses the injection of a sperm cell sample in one or more locations within the female reproductive tract. By way of example only, the sperm cell sample can be injected in one or more locations within the uterus of a sow, including one or more uterine horns, oviducts, ampulla, isthmus or utero-tubal junction. In another embodiment of the invention, embryos or zygotes can be inserted or withdrawn from a sow's reproductive tract via laparoscopy.

With respect to insemination via laparoscopy, it is contemplated that a dose of $1 \times 10^9$ sperm cells or less is administered to a sow. Such sperm cells may be sex-selected sperm cells. In one embodiment of the invention a dose of about $500 \times 10^6$ sex-selected sperm cells or less can be injected into one or both oviducts (e.g., $250 \times 10^6$ sperm cells in each oviduct) of a sow by laparoscopy; in other embodiments, doses in the range of or anywhere in between about $10 \times 10^6$, about $5 \times 10^6$, about $3 \times 10^6$, about $2.0 \times 10^6$, about $1.2 \times 10^6$, about $1 \times 10^6$, or $0.6 \times 10^6$ sex-selected sperm cells or less can be injected into one or both oviducts of a sow.

In a further embodiment, sex-selected sperm cells can be injected into specific regions of the oviduct, including but not limited to the isthmus, the ampulla and/or the utero-tubal junction. In certain embodiments, a dose in the range of or anywhere in between about $5 \times 10^6$, about $2 \times 10^6$, about $1 \times 10^6$, about $600 \times 10^3$, about $500 \times 10^3$, about $300 \times 10^3$, or about $150\times10^3$ sex-selected sperm cells or less, can be injected into one or more regions of the oviduct, either unilaterally or bilaterally.

In a further embodiment with respect to insemination via laparoscopy can be multiply injected at various sites in the oviduct using doses in the range of or anywhere in between about $500\times10^3$ sex-selected sperm cells injected into each ampulla with about $1\times10^6$ sex-selected sperm cells injected into each utero-tubal junction; or a dose of about $1\times10^6$ sex-selected sperm cells injected into each ampulla with about $2\times10^6$ sex-selected sperm cells injected into each utero-tubal junction; or a dose of about $5\times10^5$ sex-selected sperm cells injected into each ampulla with about $2\times10^6$ sex-selected sperm cells injected into each utero-tubal junction; or a dose of about $5\times10^5$ sex-selected sperm cells injected into each ampulla with about $1\times10^6$ sex-selected sperm cells injected into each utero-tubal junction. The aforementioned doses can be contained in various volumes, by way of example, 100 μl for every $1\times10^6$ million sperm cells, or the same number of sperm in one of the following or in any volume between: 50 μl, 100 μl, 200 μl, 300 μl, 400 μl or 500 μl.

Another aspect of the invention comprises synchronizing estrus and/or inducing timed ovulation in a sow that is to be inseminated using the embodiments disclosed herein by administering one or more hormone or hormone analogs to the sow. In one embodiment, the one or more hormone or hormone analogs comprises PG600 (comprising pregnant mare's serum gonadotropin, "PMSG" and human chorionic gonadotropin, "hCG"; Intervet), OvuGel (triptorelin acetate in a slow release formula via an intravaginal delivery system; Gel Med Sciences, Inc.), equine chorionic gonadotropin, "eCG," hCG, or progestin.

In a further embodiment of the invention, said one or more hormone or hormone analogs is administered by a programmable device placed in the reproductive tract of said sow. The programmable device contemplated herein is able to release said one or more hormone or hormone analogs in a time released fashion without the breeder having to monitor the device or provide any input other than programming the initial parameters for release of said one or more hormone or hormone analog. In another embodiment of the invention, estrus synchronization/timed ovulation can be induced in a sow by administering 1250 to 1500 IU of eCG and then 750 IU of hCG 72 to 80 hours later. In another embodiment, estrus can be induced in a sow by administering 400 to 2000 IU of PMSG and then 500 to 1000 IU of hCG is administered 72 to 83 hours later.

Other embodiments further contemplate detecting ovulation in a sow by examining said sow's follicles. In a particular embodiment of the invention, said sow's follicles are examined using ultrasound. In a further embodiment, said sow's ovaries are examined by transrectal ultrasound every 3-5 hours beginning 25-35 hours after hCG injection for the presence of pre-ovulatory follicles. In a further embodiment of the invention, sows showing multiple pre-ovulatory follicles are selected for insemination 2-3 hours after ultrasound.

The invention additionally encompasses a method of increasing the number of offspring of genetically superior boars in a swine herd or on a swine farm comprising establishing a subpopulation of one or more genetically superior boars from a population of boars in a herd or on a farm; obtaining sperm cell samples from the one or more genetically superior boars; preparing a plurality of sperm cell doses from each of the sperm cell samples; administering one or more hormone or hormone analogs to a plurality of sows in said herd or on said farm in order to establish a known time of ovulation for each sow; and inseminating the sows with one or more sperm cell doses using a deep intrauterine catheter or a laparoscopic procedure, wherein the one or more sperm cell doses administered to each sow together comprise a total of less than $1\times10^9$ sperm cells. These steps can also be used to reduce the number of boars necessary for breeding in a swine herd or on a swine farm. In certain embodiments, genetically superior boars comprise boars with a higher selection index relative to other boars within the herd or on the farm.

The invention also encompasses a novel method for increasing the profitability of a swine herd or farm comprising calculating a net income per pig for a male pig and for a female pig based on market conditions to which the herd or farm is subject; determining whether the male pig or the female pig results in a higher net income per pig; collecting a semen sample from a boar; sorting said semen sample into at least two subpopulations of sperm cells, wherein at least 80% of a first subpopulation bears (i) X-chromosomes if the female pig results in a higher net income per pig, or (ii) Y-chromosomes if the male pig results in a higher net income per pig; inseminating a sow with sperm cells from said first subpopulation; and producing offspring from said sow.

As used herein, the term "sow" encompasses gilts (young female pigs that have not yet farrowed) as well as any reproductively mature female pig.

Any of the embodiments of the invention can utilize a sow that is a member of a genetic nucleus or multiplier herd. Similarly, any embodiment of the invention can utilize a boar that is a member of a genetic nucleus or multiplier herd.

DETAILED DESCRIPTION OF THE INVENTION

Embodiments of the invention are directed to methods of increasing the rate of desirable genetic change or progress in a herd or line of swine through the use of sex-selected sperm samples for insemination. The use of sex-selected sperm cells produces offspring that have a high probability of being either all male or all female, depending on the separated subpopulation that is used. As shown below, this ability provides a significant advantage in the swine breeding industry since that industry greatly values annual genetic progress. An additional benefit of the use of sex-selected sperm cells is a reduction in the operational costs associated with maintaining infrastructure and materials for both sexes—e.g., the need for separate housing for male and female swine is eliminated or greatly reduced as well as the need to maintain two different supply chains for feed for males and females (males are typically fed feed that is higher in protein). A farm whose business is to sell either boars or gilts exclusively can essentially double their productivity using sex-selected sperm cells for insemination. Alternatively, they can reduce their adult herd inventory by 50% and hence reduce the working capital investment required. Enabling the use of sex-selected sperm cells in swine also allows a breeder to increase or decrease a trait in a given litter or herd of swine if that trait is expressed, or expressed more strongly, in one sex versus the other. For example, males are often castrated on commercial farms in order to reduce "boar taint" of the meat—thus, the ability to produce only females eliminates the need for castration and completely eliminates the problem of "boar taint."

The process of producing sex-selected sperm cell samples, however, is time consuming and expensive, typically requiring the use of specialized flow cytometry equipment, highly trained technicians and complex processes. Unfortunately, the typical dose of boar sperm cells required for successful fertilization using conventional artificial insemination techniques such as intra-cervical insemination is $1 \times 10^9$ sperm cells to $3 \times 10^9$ sperm cells, with the typical boar ejaculate containing approximately $6 \times 10^{10}$ sperm cells. Therefore, the typical boar ejaculate contains approximately 20 to 60 artificial insemination doses, greatly limiting the commercial application of sex-selected sperm cell samples in breeding swine. Furthermore, females are inseminated a minimum of two times per estrus cycle. Accordingly, if the total number of sperm cells needed for successful fertilization can be reduced, a greater number of artificial insemination doses can be produced for a given boar in a given amount of time, making the use of sex-selected sperm cell samples much more desirable from a commercial standpoint. In order to optimize the commercial application of sex-selected sperm cell samples in swine, the instant invention also encompasses methods for reducing the total number of sperm cells in a sample needed for an efficacious artificial insemination dose, including insemination via deep intra-uterine catheter and laparoscopy. A reduced number of sperm cells required for successful fertilization produces the additional benefit of reducing the number of boars, and their associated costs, needed for breeding.

A. Increasing the Rate of Genetic Change

By using the instant invention to select the sex of the offspring in a line, the rate of desirable genetic change of a herd or line can be increased. Genetic change, or genetic progress, in this context means that for a given trait, the individuals in the successive generation will express the desired trait more strongly than the previous generation. With respect to undesirable traits, genetic progress means the individuals in the successive generation will express the trait less strongly than the previous generation.

Genetic progress from one generation to the next (ΔG) can be measured as the difference between the average genetic level of selected parents and the average genetic level of the selection candidates (the animals available for selection). In ideal conditions, this depends upon the heritability ($h^2$) of the trait and the difference between the average performance of selected parents (P) and that of selection candidates (A). The difference between the average performance of selected parents (P) and that of all selection candidates (A) (of which the selected parents are a subset) is also known as the selection differential (SD).

$$\Delta G = h^2(P-A)$$

The sign in front of the selection differential indicates the direction of selection—a positive value indicates selection for larger phenotypic values while a negative selection differential would indicate selection for smaller phenotypic values. Thus, if the goal is selection for larger phenotypic values, individuals with large positive selection differentials relative to other individuals within the line, breed and/or herd are deemed to be superior individuals and can be selected as parents on that basis. Similarly, if the goal is selection for smaller phenotypic values, individuals with large negative selection differentials relative to other individuals within the line, breed and/or herd are deemed to be superior individuals and can be selected as parents on that basis.

Selection is more effective when non-genetic effects are removed (e.g. by comparing each performance record to the average of the contemporary group) and when information from relatives is used in addition to that of the animal itself. This is achieved through the computation of estimated breeding values (EBVs). When selection is based on EBVs, the expected genetic progress is equal to the difference between the average EBV of the selected animals and that of the selection candidates.

$$\Delta G = P_{EBV} - A_{EBV}$$

The annual rate of genetic progress is then: $\Delta G/t = (P_{EBV} - A_{ESV})/t$, where t is the generation interval. In other words, the annual rate of genetic progress depends on the generation interval and on the superiority of the parent's EBVs compared to that of the selection candidates. In certain embodiments of the invention, a statistical model such as best linear unbiased prediction (BLUP) can be used to determine EBVs, although any statistical model known in the art can be implemented for use with the invention.

Typically, when breeding swine, more than one trait is selected for. When there are multiple traits to be selected for, however, selection must be balanced for each trait depending on their economic values, how well they respond to selection (heritability) and how they influence each other (genetic correlations). One way to achieve such a balance is to create a selection index, which depends on the above values and the EBVs for each trait for each animal. The prediction of genetic progress for a selection index is the same as for an individual EBV, i.e., the annual rate of change in the index is a function of the generation interval and of the difference between the index of selected parents and the index of selection candidates.

In a large population, the selection differential depends upon how many animals are tested and how many are selected—the lower the proportion selected the higher the selection differential. Thus, in order to maximize genetic progress, one should rank all tested animals based on the selection index and then select the minimum number of top boars and sows required to maintain the line, breed and/or herd size. This ensures that the average index of selected animals is substantially higher than the average index of all animals tested.

As shown above, genetic progress is dependent on identifying superior individuals as parents for the next generation. There are two methods used to measure the phenotypic superiority of a selected individual: selection differential, as discussed above, and selection intensity. The two measures are closely related for traits with values distributed as expected for the normal distribution. The selection differential is equal to the product of the selection intensity and the phenotypic standard deviation. Because selection intensity is in standard deviation units, it is possible to compare selection pressures for different traits regardless of the type of units used to measure performance.

Additionally, one can convert the proportion of candidates selected as parents into selection intensity, since there is a direct relationship between proportion of a population and number of standard deviations between means in a normal distribution. Thus, the smaller the proportion of the population selected, the larger the selection intensity and the larger the genetic progress, all else being equal.

Furthermore, in order to achieve a greater rate of genetic progress, one would also want to keep the generation interval small—generation interval is the average age of parents in the herd when their progeny are born and can be decreased through faster replacement of boars and sows in the line, breed and/or herd. To keep the generation interval low in swine, boars should be culled before they are one year of age and sows after one or two farrowings. Finally, in order to increase genetic progress, the selected trait or traits should have a high level of heritability. The heritability of a trait is the proportion of observable differences in a trait between individuals within a population that is due to genetic, as opposed to environmental, differences.

Examples of important traits in the swine industry are feed efficiency, i.e., a measure of an animal's efficiency in converting feed mass into increased body mass (also known as feed conversion or feed to gain ratio), and average daily gain, i.e., the average daily weight gain for an animal. Traits are measured in different units (e.g., number of pigs, pounds per day, inches, etc.), are not of equal economic importance in all global markets and are not genetically influenced to the same degree (i.e., different heritabilities). Generally speaking, production traits such as feed efficiency and average daily gain have high heritability. In contrast, reproductive traits such as fertility and litter size generally have low heritability.

In certain embodiments of the invention, the efficiency with which a boar's sperm cells can be separated into X-bearing and Y-bearing subpopulations is a trait that can be selected for in a line, breed or herd. Increased expression of this trait allows the X-bearing and Y-bearing subpopulations to be sorted at an increased rate and/or with higher purity levels as compared to the average for individuals in the line, breed and/or herd, all else being equal. Certain features of a boar's semen sample can be measured to assess the efficiency with which its semen can be sorted, including the number of dead sperm in the unprocessed ejaculate, as well as how well the sperm cells take up a DNA-selective dye, such as Hoechst 33342, to create saturation of the staining process used when sorting with a flow cytometer. The number or percentage of dead sperm cells in a semen sample can be assessed using a colored or fluorescent dye that preferentially binds to damaged or dead cells, for example. Superior dye saturation is associated with a superior split of the X- and Y-chromosome bearing subpopulations as observed on the flow cytometer and/or a superior "peak to valley" ratio for the histograms generated for the X- and Y-chromosome bearing subpopulations by the flow cytometer.

Swine production can be represented by a multilevel pyramid, with certain offspring at each level used in the next lower level for breeding. The top level of the pyramid is the nucleus herd. The next levels from top to bottom are the daughter nucleus herd, the multiplier herd and finally the commercial farm, respectively.

A nucleus herd is typically comprised of 12 to 15 lines, although any number of lines may be represented, with each line comprising a number of desirable traits.

Each line can also be assigned its own selection index based on traits selected by a breeder for that line, against which offspring within each line are assessed—offspring having a higher selection index score being more desirable. As noted above, the selection index for a particular swine can be calculated using individual data or group data. The purpose of a selection index is to assign appropriate emphasis to each of the various traits to provide a single value for use in comparing different animals. Only the offspring with the highest measured selection index are retained in the nucleus herd. Sows within each line are either boar-line mothers, i.e., used to produce males, or gilt-line mothers, i.e., used to produce females. Female offspring of boar-line mothers are discarded. Likewise, male offspring of gilt-line mothers are discarded.

Accordingly, using sex-selected sperm cells of the invention for insemination, the offspring of boar-line sows have a greater chance of being male and the offspring of gilt-line sows have a greater chance of being female as compared to using conventional, unsorted semen, thereby significantly raising the selection intensity of the respective lines since there is a larger population of offspring of the correct sex to measure and then select parents from. For example, a sperm cell sample taken from a boar-line boar can be separated using the techniques disclosed herein to create a subpopulation in which at least 80% of the sperm cells bear Y-chromosomes (when using the invention on a gilt-line, a subpopulation in which at least 80% of the sperm cells bear X-chromosomes can be used). That subpopulation, or a portion of that subpopulation, can then be used to inseminate a boar-line sow. Because there is at least an 80% chance the offspring from that sow will be males, the selection intensity of the boar-line will be increased since there will be more males to select from.

At the daughter nucleus level or "line multiplication" level, sows from a line are inseminated with boar semen derived from the nucleus herd. At the multiplier herd level, the resulting sows are typically crossed with boars of a different line. A multiplier herd is typically either a gilt multiplier or boar multiplier. Gilt multipliers produce parent gilts and boar multipliers produce parent boars. Parent gilts are sent to commercial farms to replace old or dead gilts and sows, and parent boars are sent to boar studs to produce the sperm cells for use in artificial insemination.

B. Changing the Expression of Traits Across a Litter or Herd

As noted above, the use of sex-selected semen in swine breeding allows one to increase (or decrease) the expression of certain traits in a given litter or herd if those traits are expressed, or expressed more strongly, in one sex versus the other.

For example, gilts have higher feed conversion than barrows (male pigs that have been castrated before sexual maturity). Since feed costs represent a significant proportion of the cost of swine production, having litters comprised of all or substantially all females may result in increased profitability for the breeder or farm depending on local market conditions. Furthermore, compared to barrows (young castrated males), gilts (young females) generally have lower body weight, lower average daily gain, lower average daily feed intake and are leaner (less backfat depth, increased loin depth, higher fat-free lean index). Thus, although gilts may grow more slowly than barrows, they will be leaner and more efficient and thus may be more profitable for a farm under the right market conditions.

Accordingly, the use of sex-selected semen in swine can allow one to increase the profitability of a farm by selecting the sex having the most desirable traits under the market conditions.

Example 1—Preparation of Sex-Selected Boar Sperm Cell Samples

The following process for the preparation of a sex-selected boar sperm cell sample is provided by non-limiting example only. The first step in the manufacture of sex-selected boar sperm cell sample is to obtain an ejaculate from a suitable boar. Once the ejaculate has been collected, it can be extended in a suitable extender, that may include an antioxidant. A sperm rich fraction of the ejaculate can then be diluted. If the sample needs to be transported prior to sex-selection, the sample can be held at a temperature of 0-39° C. (typically 16-17° C.) for between about 12 hours to about 18 hours while it is being shipped from the collection point to the flow cytometer for the sex-sorting process.

Once the sperm cell sample is in the laboratory, various quality checks can be conducted on the sperm cell sample including checking the motility (e.g., via CASA System), viability (e.g., via flow cytometer), morphology (e.g., via microscopy) and concentration (e.g., via NucleoCounter). Sperm cell samples that pass these quality checks are then prepared for sorting.

Prior to putting the sample through the flow cytometer, the sample is stained with a DNA selective dye, exposed to a quenching dye to form a stained sperm cell sample, which is subsequently placed into a sperm cell source of the flow cytometer. Specifically, the sperm cell sample in some embodiments, can be first diluted with a buffer or extender, such as BTS (see Table 1) to a final concentration which in some cases can be $100 \times 10^6$ cells/ml, and the DNA selective dye Hoechst 33342 (can be 5 mg/ml in MiliQ water; Ref: B-2261) is then added, a good working concentration can be about 5 µl/100 million cells/ml but DNA dye can be used at lower and higher concentrations in the range of 0.5 to 20 ul/100 million cells/ml. The sample is then usually placed in covered bath water between 30 and 42° C. (usually close to 35° C.) for between 10 min and 12 hours, with exceptional staining at about 50 minutes, and then subsequently placed in a dark area at room temperature (21-22° C.) prior to sorting. Before sorting the sample, the sample is filtered to remove large debris and cells (for example with CellTricks of 0.30 µm) and after filtering, red food dye may be added (when added, usually 0.5-5 µl or 1 µl of a 25 mg/ml stock solution in MiliQ water) or another quenching dye, can be added to the sample. The sample can then be sorted using a flow cytometer with a sheath fluid which in some cases may comprise the components as listed in Table 2, but other sheath fluids may be used as well.

Figure 1:
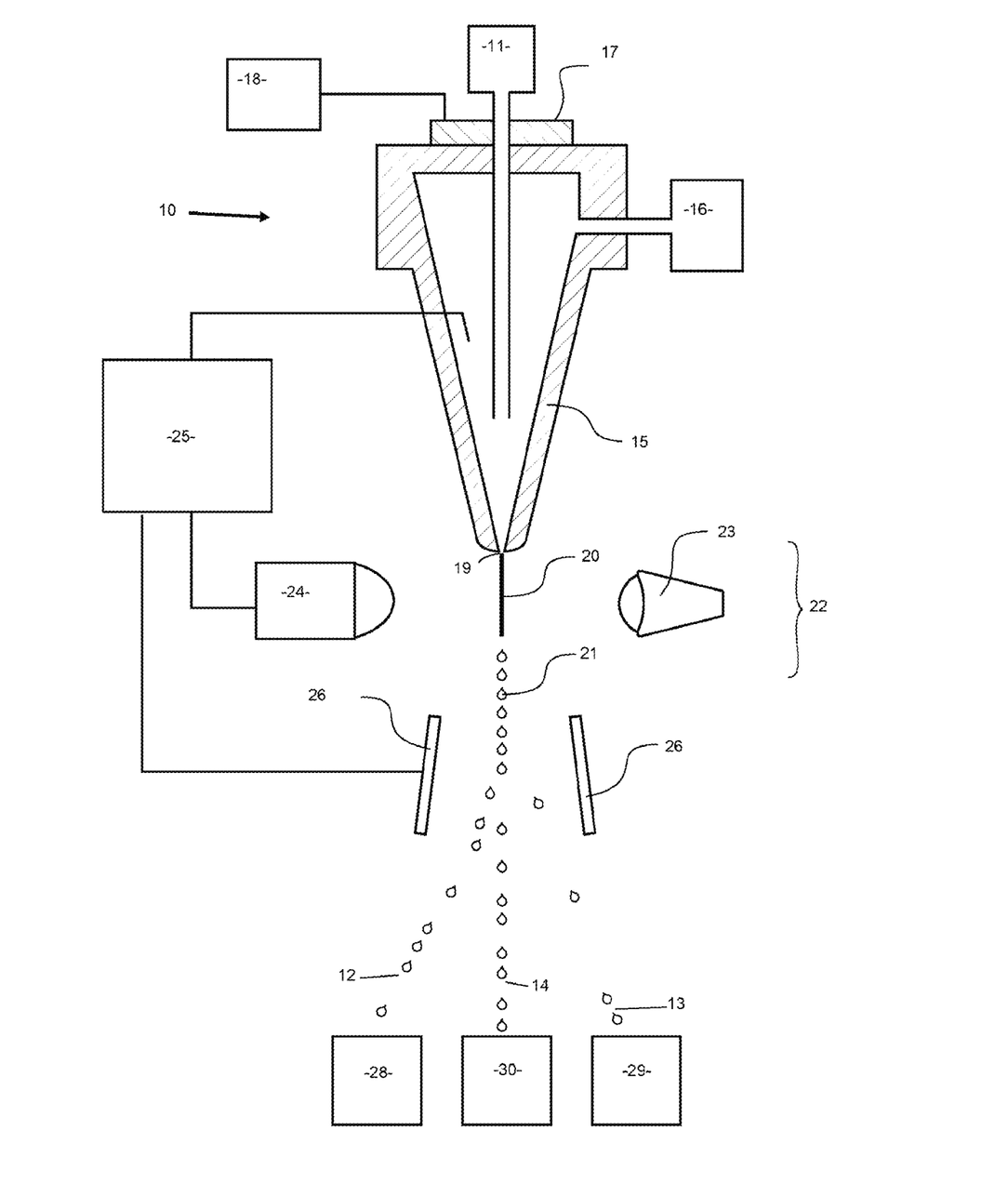
FIG. 1 illustrates schematically a flow cytometer that can be used to sort sperm cell samples into one or more subpopulations bearing X- or Y-chromosomes.

FIG. 1 illustrates, in schematic form, part of a flow cytometer used to sort a sperm cell sample to form one or more subpopulations, the flow cytometer being generally referenced as 10. In this particular embodiment, sex sorting is taking place, so the subpopulations are X-chromosome bearing sperm cells and Y-chromosome bearing sperm cells. FIG. 1 represents a single technique for sorting sperm, but any known technique for sorting cells known in the art can be used with certain embodiments of the invention.

The flow cytometer 10 of FIG. 1 can be programmed by an operator to generate two charged droplet streams, one containing X-chromosome bearing sperm cells, charged positively, 12, one containing Y-chromosome bearing sperm cells, charged negatively 13 while an uncharged undeflected stream of dead cells 14 simply goes to waste.

An operator may also choose to program the flow cytometer in such a manner, that both the X- and Y-chromosome bearing sperm are collected using a "high purity sort" (in other words only live X- and Y-chromosome bearing sperm are collected) or to program the flow cytometer to collect both the X- and Y-chromosome bearing sperm using an "enriched sort" (in other words it will collect droplets containing live that were not previously sorted and excluding all initial dead again by the use of Boolean Gate logic available with the computer that controls the flow cytometer). The Boolean Gate logic can also be used to collect only one of either the X- or Y-chromosome bearing sperm.

Initially, a stream of sperm cells under pressure, is deposited into the nozzle 15 from the sperm cell source 11 in a manner such that they are able to be coaxially surrounded by a sheath fluid supplied to the nozzle 15 under pressure from a sheath fluid source 16. An oscillator 17 which may be present can be very precisely controlled via an oscillator control mechanism 18, creating pressure waves within the nozzle 15 which are transmitted to the coaxially surrounded sperm cell stream as it leaves the nozzle orifice 19. As a result, the exiting coaxially surrounded sperm cell stream 20 could eventually and regularly form droplets 21.

The charging of the respective droplet streams is made possible by the cell sensing system 22 which includes a laser 23 which illuminates the nozzle exiting stream 20, and the light emission of the fluorescing stream is detected by a sensor 24. The information received by the sensor 24 is fed to a sorter discrimination system 25 which very rapidly makes the decision as to whether to charge a forming droplet and if so which charge to provide the forming drop and then charges the droplet 21 accordingly.

A characteristic of X-chromosome bearing sperm is that they absorb more fluorochrome dye than Y-chromosome bearing sperm because of the presence of more DNA, and as such, the amount of light emitted by the laser excited absorbed dye in the X-chromosome bearing sperm differs from that of the Y-chromosome bearing sperm and this difference communicates to the sorter discrimination system 25 the type of charge to apply to the individual droplets which theoretically contain only a single X- or Y-chromosome bearing sperm cell. Dead cells (or those about to die) typically absorb the quenching dye which is communicated to the sorter discrimination system 25 not to apply a charge to the droplets containing such cells.

The charged or uncharged droplet streams then pass between a pair of electrostatically charged plates 26, which cause them to be deflected either one way or the other or not at all depending on their charge into respective collection vessels 28 and 29 to form respectively a gender enriched population of X-chromosome bearing and a gender enriched Y-chromosome bearing sperm cells having a DNA selective dye associated with their DNA. The uncharged non-deflected sub-population stream containing dead cells (or those about to die) go to the waste container 30.

The sex-selected sperm cell sample is collected in a 50 ml tube with 2.5 ml of catch fluid, which in some embodiments can be TesTrisGlucose (TTG) (see Table 3) with 2% of egg yolk, for every 20 million cells. In this embodiment, the sex-selected sperm cell sample will typically have a final volume of approximately 24 ml at about $1 \times 10^6$ cells per ml. This tube is then stored at room temperature in a dark room for about 2 hours.

TABLE 1

| BTS Extender | | |
|---|---|---|
| CHEMICALS | SYGMA CODE | g/liter |
| Glucose | G6152 | 36.941 |
| Sodium Citrate | S4641 | 5.999 |
| Sodium Bicarbonate | S5761 | 1.261 |
| EDTA | ED2SS | 1.250 |
| Potassium Chloride | P3911 | 0.7456 |
| Kanamycin sulfate | K4000 | 0.05 |

TABLE 2

| Sheath Fluid (PBS) | | |
|---|---|---|
| CHEMICALS | SYGMA CODE | g/liter |
| Sodium Chloride | S9888 | 8 |
| Potassium Chloride | P3911 | 0.2 |
| Sodium phosphate monobasic monohydrate | S9638 | 0.12 |
| Sodium phosphate dibasic heptahydrate | S9390 | 1.717 |
| EDTA acid | E6758 | 1 |
| Penicillin G potassium salt | PENK | 0.058 |
| Streptomycin Sulfate | S6501 | 0.05 |

TABLE 3

| TesTrisGlucose (TTG) | | |
|---|---|---|
| CHEMICALS | SYGMA CODE | g/100 ml |
| TES | T1375 | 5 |
| TRIS | T1503 | 0.68 |
| GLUCOSE | G6152 | 0.6 |
| KANAMICYN | K4000 | 0.005 |

Once the sex-selected sperm cell sample has been obtained, it can be used with conventional artificial insemination procedures, such as intra-cervical insemination, in vitro fertilization or artificial insemination with deep intra-uterine catheter or laparoscopy. Alternatively, the sex-selected sperm cell sample can be cryopreserved for storage and then subsequently thawed out for use at a later time.

Example 2—Cryopreservation of Sex-Selected Boar Sperm Cell Samples

Once the sex-selected boar sperm cell sample has been manufactured, the sperm cell sample can be optionally cryopreserved for transport or storage for use at a later time. The following method of freezing can be used with the invention but is presented by way of example only—any cryopreservation method known in the art can be used.

After sorting, the 50 ml tubes containing the sex-selected sperm cells (with 20 million cells) can be divided into tubes of 15 ml, with approximately 12 ml of a sex-select sperm cell sample semen in each tube, each containing approximately 10 million sex-selected sperm cells. Theses tubes can be centrifuged at 3076 g at 21° C. for 4 minutes. The supernatant decanted, and the pellet can remain with some of the supernatant in approximately 50 µl.

To each pellet, a first freezing medium, that may comprise a solution of 20% egg-yolk and 80% β-Lactose, can then be added at room temperature. The motility of the sperm cells can then be checked. If acceptable, the tubes can be taken to a programmable temperature control machine (Poly-Science—MiniTube) or can be manually handled to decrease the temperature from about 21° C. to about 5° C. over a period of about 2 hours. After the timed temperature shift, the samples can be placed in a cold room at about 5° C. where a second freezing medium, which may comprise egg-yolk, β-Lactose, Glycerol and Equex Stem, or may just comprise a cryopreservative such as glycerol, or the cryopreservative with an osmotic stabilizer which is previously cooled to 5° C. is added to the samples. After 10 minutes, the sex-selected sperm cell samples can be placed in artificial insemination straws, and the straws then exposed to liquid nitrogen vapors (approximately 4 cm from the liquid nitrogen) for a short period of time (e.g. 10 minutes) and then placed directly into the liquid nitrogen for long term preservation.

When the sex-selected semen samples are ready for use, the straws can be unfrozen by thawing/warming the straws (e.g. place in a water bath set at about 37° C. for about 15 seconds). Post-thaw, motility and viability of the sperm cells can then be analyzed at 30, 90 and/or 150 minutes for standard comparisons.

Example 3—Estrus Synchronization

The invention contemplates that for convenience purposes, estrus can be synchronized and/or timed ovulation induced in one or more sows to be inseminated. Furthermore, because sex-selected sperm is often pre-capacitated, it is important to inseminate a sow within approximately 6 hours of ovulation. Synchronized estrus or timed ovulation helps assure this will be the case. Generally speaking this entails administering one or more hormone or hormone analogs to the sow(s) to be inseminated. There are several ways to induce estrus/timed ovulation in gilts, which are described below.

The one or more hormone or hormone analogs can be administered to the sow in order to establish estrus synchronization as well as time of ovulation. These hormones and hormone analogs typically include, for example, PG600, OvuGel, eCG, hCG, and/or progestin, and can be administered manually with timed injections or with the assistance of a programmable device placed in the reproductive tract of the sow. The programmable device contemplated herein releases one or more hormone or hormone analogs in a time released fashion without the breeder having to monitor the device or provide any input other than programming the initial parameters for release of said one or more hormone or hormone analogs. Any of the following methods for inducing and/or synchronizing estrus known in the art may be used generally with the invention, including the following.

(a) Transport and Boar Induced Estrus. Gilts typically attain puberty at approximately 180-210 days of age. However, the natural attainment of puberty is influenced by many intrinsic and extrinsic factors, such as genotype, environment and boar contact. Many breeders and farmers indicate that the first estrus is commonly observed when gilts are six months of age. The onset of estrus often coincides with relocation or transport of animals from the gilt multiplier to the commercial farm. Undoubtedly, the best-known stress factor in pigs is that of transportation. If the age of gilts at the time of transport is close to the normal onset of puberty, approximately 25-35% of gilts will display estrus within one week after transport. This transport-induced estrus can serve to synchronize a proportion of gilts.

Although transport may induce estrus, it is evident that boar contact is a potent form of puberty stimulation. The major factor controlling the efficiency of boar contact as a puberty stimulus is the age of the gilt at the time of boar introduction. When boar contact is initiated when gilts are 4 months of age, the pubertal response is minimal. It was suggested that the young gilt may become habituated to the boar stimulus at a stage in development when she is too young to respond. Conversely, when boar introduction is delayed until the immediate prepubertal period (6 months of age and above), the response is again limited for a different reason. By virtue of the relatively old ages, i.e. 6 months, of gilts at introduction, the actual pubertal ages of these gilts are not much reduced below those of unstimulated animals. When boar introduction occurs at gilt ages in the region of 160 days, both the interval from first boar contact to puberty and gilt age at puberty are minimized, while maximum synchronization of the pubertal estrus occurs.

(b) Oral and Time-Release Progestins. This approach to estrus synchronization utilizes suppression of ovarian activity through the administration of orally administered progesterone or synthetic progestins. Some progestins can be obtained that are timed-release injectible forms, such as altrenogest (see below). Feeding cyclic gilts individually or in groups at a rate of 15-30 mg altrenogest/pig/day for 14 to 18 consecutive days produces a synchronous onset of estrus between 2 and 8 days after the last progestin feeding.

(c) Gonadotropins. eCG/hCG (PG600R) Presently, the most common exogenous hormone combination for induction of follicle growth and ovulation in acyclic females is a combination of eCG, formerly called pregnant mare's serum gonadotropin (PMSG), and human chorionic gonadotropin (hCG). The product PG600R contains 400 IU PMSG and 200 IU hCG. This hormone can be purchased as a combination drug and is cost-effective for the induction of estrus and ovulation in acyclic pigs. Gilts usually show estrus 3-6 days after treatment and the time of ovulation is approximately 110-120 hours. The response rate is enhanced if gilts are given daily boar contact, beginning at the time of treatment. PG600 comprises pregnant mare's serum gonadotropin, otherwise known as equine chorionic gonadotropin ("PMSG" or "eCG") and human chorionic gonadotropin ("hCG") (Intervet). OvuGel is another commercially available gonadotropin (triptorelin acetate) in a slow release formula which can be administered via an intravaginal delivery system (Gel Med Sciences, Inc.).

(d) Prostaglandins. $PGF_2$ alpha is effective for inducing luteolysis, abortion, and a prompt return to estrus in pregnant (and pseudopregnant) gilts beyond the second week of pregnancy. One method for synchronization is to pen-mate gilts for three weeks and then, treat with $PGF_2$ alpha two weeks later.

(e) Time-Release Hormones. Another method involves the direct injection of a commercially available preparation, such as altrenogest or regumate, at a specific time point in the estrus cycle. For example, in one embodiment of the invention, synchronization and timed ovulation is achieved by administering on day 11-14 of a gilt's estrus cycle, 15-30 mg altrenogest/day for 4 to 7 days. 24 hours after stopping altrenogest, 400 to 2000 IU of PMSG can be administered, and then 500 to 1000 IU of hCG, 72 to 83 hours later.

Example 4—Ovulation Detection

Ovulation detection in a sow can be done by examining the sow's follicles. The realization of the importance of establishing an adequate sperm reservoir in the oviduct at an appropriate time relative to ovulation is critical in the management of artificial insemination in swine. In particular, knowledge of when a sow is likely to ovulate during estrus is highly beneficial to achieving successful insemination. To that end, in a particular embodiment of the invention, sow's follicles are examined using ultrasound after the induction of estrus. In a specific embodiment of the invention, the sow's ovaries are examined by transrectal ultrasound every 4 hours beginning 30 hours after hCG injection for the presence of pre-ovulatory follicles. Sows showing multiple pre-ovulatory follicles (diameter of antrum>6 mm) are selected for insemination 2-3 hours after ultrasound.

Example 5—Insemination Using Laparoscopy or Deep Intrauterine Catheter

Once the sex-selected boar semen sample has been prepared, the sample can be used to inseminate a sow. Any conventional artificial insemination technique can be used in the invention, including intra-cervical insemination. However, deep intrauterine catheters and laparoscopy are particularly relevant in swine, since they allow for the use of a reduced dose of sperm cells for successful fertilization, in part because they are able to place the sperm cells in key areas of the sow's reproductive tract, including but not limited to the uterine horns, the oviducts, the ampulla, the isthmus and the utero-tubal junction. The use of reduced sperm cell doses allows the use of far fewer genetically superior boars for breeding purposes, which has the benefits of reducing costs to breeders and reducing the environmental harm that results from having to maintain a large number of boars.

(a) Insemination Using Deep Intrauterine Catheter. The use of a deep intrauterine catheter allows one to place sperm cells into the uterine horns of the sow and ideally at the utero-tubal junction. The use and construction of such a deep intrauterine catheter is disclosed in U.S. Pat. No. 6,695,767, the disclosure of which is hereby incorporated by reference in its entirety. Such a deep intrauterine catheter can optionally comprise a video camera or scope to allow the operator to see the path of the catheter, so that a choice between placing sperm cells in one or both of the uterine horns can be made. Alternatively, the location of the deep intrauterine catheter can be visualized within a reproductive tract of a sow when used in conjunction with a radiographic or fluoroscopic device. Because of its length, a deep intrauterine catheter allows the operator to reach distal regions of a sow's reproductive tract, including the uterine horns—regions that would be unreachable using a standard catheter used for artificial insemination. In one embodiment of the invention, the length of the deep intrauterine catheter is 1.8 m, 1-2 m, 1-2.5 m or 1-3 m.

The deep intrauterine catheter can be introduced inside of the cervical duct of a sow in estrus which may be superovulated but may also be naturally cycling or otherwise induced. A non-toxic lubricant liquid can be applied onto the catheter to facilitate its passage through the vagina. The catheter can comprise an outer tube or sheath and a flexible probe within the outer tube or sheath. In one embodiment of the invention, once the catheter has been advanced to the cervical duct, the flexible probe can be further advanced within the outer tube of the catheter. The flexible probe can be advanced until reaching the anterior portion of a uterine horn. When the flexible probe is advanced within the uterine horn, it can bend and thus continue to follow the tortuous path of the uterine horn. Although it is not absolutely necessary, introduction of small volumes of liquid through the outer tube of the catheter can facilitate progression of the flexible probe at its passage through the cervical duct and its progression through the uterine horn. Once the flexible probe has been introduced up to its final position within the uterine horn, a sperm cell sample contained in a syringe being connected to the proximal end of the flexible probe and can be introduced—through a flexible duct within the flexible probe—into the uterine environment. So as to avoid losses of sperm cells and to ensure that the sperm cell sample has been completely evacuated from the flexible duct, a small volume of liquid can be subsequently introduced through the flexible duct. Thereafter, the catheter, comprising the outer tube and the flexible probe, can be withdrawn. In another aspect of the invention, this process can also be used for transferring embryos into a uterine horn or removing embryos from a uterine horn.

(b) Insemination Using Laparoscopy. Use of laparoscopy to inseminate a sow has the advantage that the placement of sperm cells within the sow's reproductive tract can be even more precise than with the use of a catheter, thus further enabling the use of reduced sperm cell doses for insemination. Specific areas of the uterus can be targeted, such as the oviduct, the isthmus, ampulla, or the utero-tubal junction. By way of a non-limiting example, the following procedure can be used with the invention to inseminate a sow via laparoscopy.

For example, a 50 ml tube containing 24 ml of a sex-selected sperm cell sample having about $1 \times 10^6$ sperm cells per ml can be divided into 2 tubes of 15 ml and centrifuged at about 3076 g at a temperature in the range of about 21° C. for several minutes (2-5 or 4 minutes). The supernatant can be recentrifuged under the same conditions if needed. The resulting semen pellets are then mixed and the concentration checked (via NucleoCounter). The concentrated sex-selected sperm cell sample is then diluted with BTS to a final concentration of $10 \times 10^6$ cells/ml and the motility and viability of the sperm cells is checked. (The sperm cell sample should be maintained at room temperature (21° C.) during the entire process.)

Sows can be grouped or separated, for instance they can be allocated individually to stalls in a mechanically ventilated confinement facility. Sows (2-6 parity) are weaned at about 21 days. Estrus can then be induced by injecting each female intramuscularly with about 1250 IU equine chorionic gonadotrophin (eCG; Folligon, Intervet International B.V., Boxmeer, The Netherlands—or an equivalent compound) 24 hours after weaning; 72 hours later, they are treated with about 750 IU human chorionic gonadotrophin (hCG; Veterin Corion, Divasa, Farmavic S.A., Barcelona, Spain) or an equivalent. Estrus detection is performed once a day (for instance at 7:00 a.m.), beginning 2 days after eCG injection. One way to detect estrus is to allow females nose to nose contact with a mature boar and by applying back pressure, to identify sows that exhibit a standing heat reflex, which are considered to be in estrus; at which point the ovaries can be scanned. The ovaries can be examined at periodic intervals (e.g. every 4 hours) for mature follicles starting at about 30 hours after hCG injection by transrectal ultrasonography using a 5 MHz multiple scan angle transducer, to look for the presence of pre-ovulatory follicles. Only sows showing multiple pre-ovulatory follicles (diameter of antrum>6 mm) are selected for insemination. Inseminations are carried out within 2-3 h after ultrasonography.

Laparoscopic inseminations can then be performed on these sows once sedated (which may be by azaperone administration; Stresnil; 2 mg/kg body weight, i.m.). General anesthesia can also be induced with a compound such as sodium thiopental (Abbot; 7 mg/kg body weight, i.v.) and maintained with halothane (3.5-5%) or a similar compound. For surgery, the sow can be placed in the supine position, and if available, on her back in a laparoscopy cradle. If a cradle is used, it is placed in a Trendelenburg position (hind quarters upward, with the head pointing down) at an angle of approximately 20° above horizontal.

In one embodiment, an incision (about 1.5 cm) is made close to the umbilicus. The edges of the incision can then be pulled up with countertraction and a 12 mm Optiview trocar (Ethicon Endo-surgery Cincinnati Ohio, USA) with an inserted 0° laparoscope is advanced into the wound. At the umbilicus, the subcutaneous fatty tissue, the anterior fascia of the rectus muscles, the rectus muscles, the posterior fascia of the rectus muscles, the transversalis fascia and the peritoneum are traversed by slight cutting and moderate pressure. The process is controlled via monitor feedback. Although the $CO_2$ tubing is connected to the trocar, inflation does not begin until the peritoneum is punctured. After the peritoneal cavity is entered and the pneumoperitoneum started, the handpiece of the Optiview is removed and replaced by the 0° laparoscope. The abdominal cavity is inflated to 14 mmHg with $CO_2$. Two accessory ports are placed in the right and left part of the hemi abdomen, which provides access for laparoscopic Duval forceps for manipulating the uterine horn and grasping the oviduct for the insemination needle, respectively. The oviduct is grasped with the Duval forceps in the isthmus region. Then the dose-flow (containing 0.3-0.5 million of spermatozoa in 0.1 ml) is inserted, and sex sorted spermatozoa are flushed into the oviduct. The procedure is then repeated on the other oviduct. After both oviducts are inseminated, the trocars are removed, and incision wounds sutured.

Example 6—Selection Indexes

Environmental differences make it difficult to compare pigs tested at different locations, at different times, or under different management. The use of selection indexes based on contemporary group comparisons, however, removes much of the influence of these environmental factors. Thus, more valid comparisons of genetic merit are possible. Any selection index known in the art can be used as a component of the invention. The following selection indexes are provided by way of example only.

Sow Productivity Index (SPI). This index provides a measure of sow productivity and is useful when culling sows. Prolificacy is measured by the adjusted number of pigs born alive in a litter. Milking ability is measured by the adjusted weight of the litter at 21 days of age.

Early Weaning Sow Productivity Index (EWSPI). This index is designed for use in culling sows when 21-day litter weights are not available. Litter weight at 21 days is used as a correlated trait when the index is constructed, allowing some selection emphasis to be placed on milking ability even when weights are not collected.

Maternal Index (MI). The maternal index is intended to put emphasis on maternal characteristics and is useful for selecting boars to produce replacement gilts and in selecting replacement gilts. Because barrows, and gilts that are unacceptable for replacements, are residuals of this type of mating, there is some emphasis on growth rate, backfat and feed efficiency. Feed efficiency is included as a correlated trait, although it is not measured directly. In certain embodiments, it is recommended that potential replacements not be weaned before 10 days of age so that litter weight can be used to select for milking ability.

Terminal Indexes (TI). The terminal indexes put emphasis on growth, efficiency, and backfat. The terminal indexes can be used for selecting animals to be used in terminal crosses. If backfat is measured using A-mode ultrasound, the TI-A should be used. If backfat is measured with B-mode ultrasound or metal probe, the TI-B is the appropriate index. The TI-M is for use if predicted percent lean has been calculated.

The above indexes will average 100 for each test group and should have a standard deviation of about 25.

The traits used in the calculation of the above selection indexes disclosed herein are defined as follows:

L=the adjusted number born alive record on the dam minus the average of the adjusted number born alive records of her contemporary group;

W=the adjusted 21-day litter weight record on the dam minus the average of the adjusted 21-day litter weight records of her contemporary group;

D=adjusted days to 250 pounds measured on the individual minus the average of the adjusted days to 250 pounds of the test group;

B=backfat measured on the individual, adjusted to 250 pounds, minus the average of the adjusted backfat of the test group; and M=predicted percent lean calculated for the individual minus the average predicted percent lean of the test group.

The number of pigs born alive should be adjusted to a mature sow equivalent by adding the following numbers to the record based on the parity of the female:

TABLE 4

Parity adjustment factors for number born alive.

| Parity | Number born alive (L) |
|---|---|
| 1 | 1.2 |
| 2 | 0.9 |
| 3 | 0.2 |
| 4-5 | 0.0 |
| 6 | 0.2 |
| 7 | 0.5 |
| 8 | 0.9 |
| 9 | 1.1 |

L=the adjusted number born alive record on the dam minus the average of the adjusted number born alive records of her contemporary group;

An individual breeder may wean at any time, but litter weight should be recorded before weaning and as near to 21 days of age as possible for the most accurate assessment of sow milking ability. Pigs should be weighed between 14 and 28 days and adjusted to a 21-day basis. Post-farrowing litter weights may be adjusted to a 21-day basis by using the following multiplicative factors:

TABLE 5

Factors for adjusting litter weight to a 21-day basis.

| Age Weighed | Factor |
|---|---|
| 10 | 1.50 |
| 11 | 1.46 |
| 12 | 1.40 |
| 13 | 1.35 |
| 14 | 1.30 |
| 15 | 1.25 |
| 16 | 1.20 |
| 17 | 1.15 |
| 18 | 1.11 |
| 19 | 1.07 |
| 20 | 1.03 |
| 21 | 1.00 |
| 22 | 0.97 |
| 23 | 0.94 |
| 24 | 0.91 |
| 25 | 0.88 |
| 26 | 0.86 |
| 27 | 0.84 |
| 28 | 0.82 |

The following equation was used to compute the tabular values and can be used to directly adjust litter weight to a 21-day basis:

Adjusted 21-day litter weight=wt.*[2.218−0.0811 (age)+0.0011(age$^2$)].

Pigs should be weaned no earlier than 10 days of age; using factors in Table 5 will permit sows to be ranked on the Sow Productivity Index. The closer to 21 days of age pigs are weaned, the more accurate the adjustment will be.

If possible, litters should be standardized to between 8 and 12 pigs per litter within 24, but not later than 48, hours after birth. Pigs selected for transfer should be average in size. Males, rather than females, should be transferred if possible. Standardization of the post-farrowing weight record will prevent discrimination against a good milking sow or gilt that has a lesser opportunity because of smaller than optimum litter size. The litter weight (already adjusted to a 21-day basis) should be standardized to 10 pigs by adding the appropriate value from the following table:

TABLE 6

Factors for adjusting 21-day litter weight for number of pigs after transfer (number allowed to nurse).

| Number of pig safter transfer | Adjustment factor for 21-day litter weight (W) |
|---|---|
| 1-2 | 104 |
| 3 | 76 |
| 4 | 61 |
| 5 | 51 |
| 6 | 41 |
| 7 | 30 |
| 8 | 21 |
| 9 | 17 |
| >=10 | 0 |

Post-farrowing litter weights should also be adjusted to a mature sow equivalent by adding the following numbers to the record based on the parity of the female:

TABLE 7

Parity adjustment factors for 21-day litter weight.

| Parity | Adjustment factor for 21-day litter weight (W) |
|---|---|
| 1 | 6.2 |
| 2 | 0.0 |
| 3 | 1.0 |
| 4 | 3.8 |
| 5 | 6.2 |
| 6 | 9.5 |
| 7 | 11.6 |
| 8 | 15.2 |
| >=9 | 21.5 |

The adjustment factors in Tables 4-7 were derived for general purpose use from large data sets. Whenever possible, specific adjustment factors should be derived from data sets for specific populations, for use in those populations specifically. Growth rates must be measured on all intact males and/or all gilts by one of two procedures.

W=the adjusted 21-day litter weight record on the dam minus the average of the adjusted 21-day litter weight records of her contemporary group;

(a) Age at a constant weight. If pigs are not weighed on test but only a final weight is taken, weights should be taken at or near 250 pounds or some other comparable constant weight. The equation for adjusting days to a constant weight is:

Adjusted days=actual age+[(desired wt.−actual wt.)* ((actual age−$a$)/actual wt.)]

(where $a$=50 for boars and barrows, and 40 for gilts).

(b) On-test gain. Pigs should be weighed on test at an average pig weight consistent with the management program of the operation. Average pig weights of approximately 70 pounds are recommended. Ranges in starting weights among individual pigs should be minimized. Off-test pig weight should average at least 160 pounds more than starting weight. If pigs being tested have undergone segregated early weaning, the test may be started at an average starting weight of 40 pounds and off-test pig weights should average at least 190 pounds more than starting weight.

D=adjusted days to 250 pounds measured on the individual minus the average of the adjusted days to 250 pounds of the test group;

(c) Backfat. All pigs should be measured for backfat thickness at the tenth rib location when they are weighed off-test at 250 pounds. The average of two measurements, taken 2 inches off the midline on both sides of the pig, should be obtained if a metal probe or A-mode ultrasound machine is used. If a B-mode (real-time) ultrasound machine is used, a single measurement is sufficient. Backfat depth should be measured at the midpoint of the loin, and should include the skin and all fat layers. If any other backfat measurements are taken, an explanation should be given. All measurements should be adjusted to a constant basis using the formula below:

Adjusted backfat=actual backfat+[(desired wt−actual wt)*(actual backfat/(actual wt−$b$))]

(where b=−20 for boars, +30 for barrows, and +5 for gilts).

B=backfat measured on the individual, adjusted to 250 pounds, minus the average of the adjusted backfat of the test group;

(d) Loin-Muscle Area. The loin-muscle area (LMA) should be measured on pigs when they are weighed off-test, within a 30 pound range of the desired weight endpoint (e.g., 250 pounds). Loin-muscle area should be measured over the 10th rib at a location 2 inches off the midline. The equation for adjusting LMA to a constant weight basis is:

Adjusted LMA=actual LMA+[(desired wt−actual wt)*(actual LMA/(actual wt+155))].

(e) Predicted Percent Lean. This trait can be used in place of backfat in a selection index. Use the following equation to calculate Predicted Percent Lean (PPL) if pigs are weighed off-test at 250 pounds:

Adjusted PPL=[80.95−(16.44*$adj\ bf$)+(4.693*$adj\ LMA$)]*0.54.

M=predicted percent lean calculated for the individual minus the average predicted percent lean of the test group.

Given the above adjustment factors, the aforementioned selection indexes can then be calculated as follows:

SPI=100+6.5($L$)+$W$

EWSPI=100+10($L$)

MI=100+6($L$)+0.4($W$)−1.6($D$)−81($B$)

TI-$A$=100−1.7($D$)−168($B$)

TI-$B$=100−1.4($D$)−106($B$)

TI-$M$=100−1.4($D$)+12($M$)

A. Selection Indexes—Using Expected Progeny Differences

The actual genetic merit of an animal is its breeding value, which is the sum effect of all its genes. How the breeding value is expressed by each pig's individual phenotype is dependent on the environmental conditions under which it is raised. The concept of breeding value relates to selection through the fact that genes occur in pairs. Selected animals transmit a sample one-half of their genes (one of each pair), or one-half of their breeding value, to each offspring. For this reason, the expected difference between the progeny of an individual and the original population is one-half the breeding value of that individual. Many genetic programs express the genetic merit estimate as expected progeny differences (EPD), which is one-half the animal's EBV. Therefore, EPD=½ EBV.

EPDs can be based on direct measures of animal performance, and/or on measures of performance of relatives to the animal in question (ancestors, siblings, progeny). To calculate EPDs, all available information can be combined in a BLUP statistical procedure. The EPD is a prediction of how progeny of an individual are expected to perform relative to the group or population average (disregarding the other parent). The EPD for progeny resulting from the mating of a specific male to a specific female is the sum of the EPDs of the two parents.

EPDs and EBVs are estimates. The more sources of information that can be used in the estimates, the more accurate these estimates will be. The reliability to be placed on the EPD is associated with the accuracy of each EPD. Accuracy is defined as the correlation between the EBV of an individual and its "true" breeding value. An accuracy value close to 1.0 indicates higher reliability for the EPD. The accuracy value reported in most genetic evaluation programs is a function of the possible change or variation for that particular trait. A producer may wish to limit the use of an animal with low accuracy, whereas a boar with many progeny and hence a higher accuracy may be used more extensively. Accuracy values are most effective as a tool for risk management because regardless of accuracy, EPDs are the best estimates of genetic value currently.

A positive EPD is desirable when selecting for traits such as number of pigs born alive or 21 day litter weights because a large positive number translates into more pigs per litter or more pounds per litter. When selecting against backfat or days to market weight, however, a negative EPD is desirable because one wishes to reduce the time required to reach market weight and the amount of backfat.

If EPDs are reported, animals may be evaluated with selection indexes similar to those listed above. The simplest index consists of all the EPDs added together. For example, if a producer is interested in litter size, growth and backfat, the index would be:

$I$=100+$EPD_L$+$EPD_D$+$EPD_B$

Use of economic values for each trait can weight the genetic information for the relative economic importance of each trait. Using the economic values of $13.50 for L, $0.12 for D, and $15.00 for B, for example (economic values given in dollars per 1 unit of change in the trait), would yield the following selection index:

$I$=(100+13.5)*($EPD_L$−0.12)*($EPD_D$−15)*$EPD_B$

B. Examples of Calculating Selection Indexes

The following are examples of calculating selection indexes are provided by way of example only.

Calculating a Maternal Index. The gilt to be indexed was born in a first parity litter of 11 and reared in a litter of 10 which weighed 178 lb at 23 days of age. Her weight at 160 days of age was 240 lb, and her B-mode ultrasound backfat reading at that weight was 0.9 inches. To calculate the index value for this gilt, her records must be adjusted to standard conditions. This gilt was born in a first-parity litter, so her dam's record for number born alive must be increased by 1.2 pigs (Table 4): 11+1.2=12.2 pigs. Since the litter was weighed at 23 days of age, the weight should be multiplied by 0.94 (Table 5). Litter weight should also be adjusted for parity by adding 6.2 lb (Table 7). No adjustment for litter size is necessary because the litter had 10 or more pigs. The final adjusted litter weight is (178*0.94)+6.2=173.5 lb.

The gilt's record for days to 250 lb is calculated using the equation as provided above. The desired weight is 250 lb, actual weight was 240 lb, actual age was 160 days, and the correction factor for gender is 40 days, giving an adjusted days to 250 lb of 165 days. Adjusted backfat is calculated in a similar manner using the above equation. The adjusted backfat for this gilt is 0.94 inches.

The adjusted values for the traits must also be calculated for all gilts in the contemporary group and averaged to yield L, W, D, and B. If the average adjusted values for this gilt's contemporary group were L=9.4 pigs, W=158 lb, D=163 days, and B=1.04 inches, her maternal index is:

$$I=100+6*(12.2-9.4)+0.4(173.5-158)-1.6(165-163)-81(0.94-1.04)=128 \text{index points}$$

Calculating a Terminal Index. Assume one wishes to determine the index of a boar that required 150 days to reach 250 lb in a contemporary group that averaged 165 days. His adjusted backfat (B-mode) was 0.6 inches and the group average was 0.75 inches. He was born and reared in a second parity litter of 9 which weighed 200 lb at 22 days. The contemporary group adjusted values for litter size and weight are 9.1 and 185, respectively. To calculate the terminal index, one uses the adjusted values already determined in the selection index for B-mode backfat scans as provided above:

$$I=100-1.4(150-165)-106(0.6-0.75)=137 \text{index points}$$

Note that one can ignore the litter information because this boar will be used to sire only market pigs. If one were interested in using him to sire replacement gilts, one would need to use the maternal index.

As can be easily understood from the foregoing, the basic concepts of the present invention may be embodied in a variety of ways. The invention involves numerous and varied embodiments using sex-selected sperm cells to increase the genetic progress of a line, breed or herd, including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "sorter" should be understood to encompass disclosure of the act of "sorting"—whether explicitly discussed or not—and, conversely, were there effectively disclosure of the act of "sorting", such a disclosure should be understood to encompass disclosure of a "sorter" and even a "means for sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation in part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation in part application thereof or any reissue or extension thereon.

What is claimed is:

1. A method of increasing the genetic progress of a line or breed of swine within a genetic nucleus comprising the steps of:
providing a boar from a genetic nucleus and a sow from a genetic nucleus, wherein said boar and said sow are from a line or breed within said genetic nucleus and wherein said line or breed of said boar and said sow are the same line or breed;
collecting a semen sample from said boar;
sorting said semen sample into at least two subpopulations of sperm cells, wherein at least 80% of a first subpopulation bears X-chromosomes or Y-chromosomes;
administering a hormone or hormone analog to said sow;
detecting ovulation in said sow;
inseminating said sow with $50 \times 10^6$ or less sperm cells from said first subpopulation by deep intrauterine catheter or by laparoscopy;
producing offspring from said sow;
calculating one or more estimated breeding values for said offspring; and
selecting one or more of said offspring as a parent in the line or breed in the genetic nucleus based on the one or more determined estimated breeding values.

2. The method of claim 1, wherein the one or more estimated breeding values are calculated by best linear unbiased prediction.

3. The method of claim 1, wherein ovulation is detected by ultrasound.

4. The method of claim 1, wherein the hormone or hormone analog is selected from the group consisting of: progesterone; a progestin; and a gonadotropin.

5. The method of claim 1, wherein said sow is inseminated with $1 \times 10^6$ or less sperm cells from said first subpopulation.

6. The method of claim 1, wherein the deep intrauterine catheter is 1 to 3 meters in length.

7. The method of claim 1, wherein said sow is inseminated laparoscopically in one or more of said sow's uterotubal junctions.

8. The method of claim 1, wherein said sow is inseminated laparoscopically in one or more of said sow's isthmus.

* * * * *